United States Patent
Chan et al.

(10) Patent No.: US 7,078,565 B2
(45) Date of Patent: Jul. 18, 2006

(54) BENZAMIDE DERIVATIVES AS ANTAGONISTS OF OREXIN RECEPTORS

(75) Inventors: Wai Ngor Chan, Harlow (GB);
Amanda Johns, Harlow (GB);
Roderick Alan Porter, Harlow (GB);
Rachel Elizabeth Anne Stead, Harlow (JP); Mythily Vimal, Harlow (GB)

(73) Assignee: SmithKline Beecham plc, Brentford (GB)

( * ) Notice: Subject to any disclaimer, the term of this patent is extended or adjusted under 35 U.S.C. 154(b) by 0 days.

(21) Appl. No.: 10/494,011

(22) PCT Filed: Oct. 30, 2002

(86) PCT No.: PCT/EP02/12170

§ 371 (c)(1),
(2), (4) Date: Sep. 16, 2004

(87) PCT Pub. No.: WO03/037847

PCT Pub. Date: May 8, 2003

(65) Prior Publication Data

US 2005/0020584 A1    Jan. 27, 2005

(30) Foreign Application Priority Data

Nov. 1, 2001    (GB) ................. 0126292.2

(51) Int. Cl.
*C07C 233/65* (2006.01)
*A61K 31/165* (2006.01)

(52) U.S. Cl. .................... 564/158; 514/307; 514/359; 514/364; 514/365; 514/403; 514/465; 514/469; 514/524; 546/146; 548/131; 548/200; 549/441; 549/465; 558/415; 560/45

(58) Field of Classification Search ............. 564/158; 558/415; 548/131, 200, 266.8; 549/441, 549/465; 560/45; 546/146; 514/524, 617, 514/364, 365, 359, 403, 465, 469, 307, 532, 514/523

See application file for complete search history.

(56) References Cited

FOREIGN PATENT DOCUMENTS

| EP | 0 500 336 | 8/1992 |
|---|---|---|
| WO | 00/20358 | * 4/2000 |
| WO | WO 00/47284 | 8/2000 |
| WO | WO 00/47576 | 8/2000 |
| WO | WO 01/68609 | 9/2001 |
| WO | WO 01/85693 | 11/2001 |
| WO | WO 01/96302 | 12/2001 |

* cited by examiner

*Primary Examiner*—Shailendra Kumar
(74) *Attorney, Agent, or Firm*—Kathryn L. Sieburth; Mary E. McCarthy; Charles M. Kinzig

(57) ABSTRACT

Disclosed are phenyl-alkylene benzamides useful as orexin antagonists

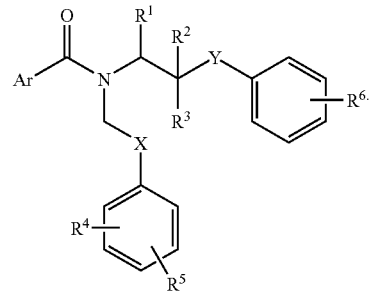

25 Claims, No Drawings

BENZAMIDE DERIVATIVES AS ANTAGONISTS OF OREXIN RECEPTORS

This application is a 371 of PCT/EP02/12170, filed Oct. 30, 2002.

This invention relates to benzamide derivatives and their use as pharmaceuticals.

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in EP-A-875565, EP-A-875566 and WO 96/34877. Polypeptides and polynucleotides encoding a second human orexin receptor, orexin-2 (HFGANP), have been identified and are disclosed in EP-A-893498.

Polypeptides and polynucleotides encoding polypeptides which are ligands for the orexin-1 receptor, e.g. orexin-A (Lig72A) are disclosed in EP-A-849361.

Orexin receptors are found in the mammalian host and may be responsible for many biological functions, including pathologies including, but not limited to, depression; anxiety; addictions; obsessive compulsive disorder; affective neurosis/disorder, depressive neurosis/disorder; anxiety neurosis; dysthymic disorder; behavior disorder; mood disorder; sexual dysfunction; psychosexual dysfunction; sex disorder; sexual disorder; schizophrenia; manic depression; delerium; dementia; severe mental retardation and dyskinesias such as Huntington's disease and Gilles de la Tourett's syndrome; feeding disorders, such as anorexia, bulimia, cachexia, and obesity; diabetes; appetite/taste disorders; satiety; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis disease; hypophysis tumor/adenoma; pituitary growth hormone; adrenohypophysis hypofunction; adrenohypophysis hyperfunction; hypothalamic hypogonadism; Kallmnan's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; circadian rhythms; and sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as sub-arachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g. HIV, post-polio syndrome, and post-herpetic neuralgia; phantom limb pain; labour pain; cancer pain; post-chemotherapy pain; post-stroke pain; post-operative pain; neuralgia; conditions associated with visceral pain including irritable bowel syndrome, migraine and angina; urinary bladder incontinence e.g. urge incontinence; tolerance to narcotics or withdrawal from narcotics; sleep disorders; sleep apnoea; narcolepsy; insomnia; parasomnia; jet-lag syndrome; and neurodegenerative disorders, which includes nosological entities such as disinhibition-dementia-parkinsonism-amyotrophy complex, pallido-ponto-nigral degeneration, epilepsy, and seizure disorders.

Experiments have shown that central administration of the ligand orexin-A (described in more detail below) stimulated food intake in freely-feeding rats during a 4 hour time period. This increase was approximately four-fold over control rats receiving vehicle. These data suggest that orexin-A may be an endogenous regulator of appetite. Therefore, antagonists of its receptors may be useful in the treatment of obesity and diabetes, see Cell, 1998, 92, 573–585.

There is a significant incidence of obesity in westernised societies. According to WHO definitions a mean of 35% of subjects in 39 studies were overweight and a further 22% clinically obese. It has been estimated that 5.7% of all healthcare costs in the USA are a consequence of obesity. About 85% of Type 2 diabetics are obese, and diet and exercise are of value in all diabetics. The incidence of diagnosed diabetes in westernised countries is typically 5% and there are estimated to be an equal number undiagnosed. The incidence of both diseases is rising, demonstrating the inadequacy of current treatments which may be either ineffective or have toxicity risks including cardiovascular effects. Treatment of diabetes with sulfonylureas or insulin can cause hypoglycaemia, whilst metformin causes GI side-effects. No drug treatment for Type 2 diabetes has been shown to reduce the long-term complications of the disease. Insulin sensitisers will be useful for many diabetics, however they do not have an anti-obesity effect.

Rat sleep/EEG studies have also shown that central administration of orexin-A, an agonist of the orexin receptors, causes a dose-related increase in arousal, largely at the expense of a reduction in paradoxical sleep and slow wave sleep 2, when administered at the onset of the normal sleep period. Therefore antagonists of its receptors may be useful in the treatment of sleep disorders including insomnia.

The present invention provides benzamide derivatives which are non-peptide antagonists of human orexin receptors, in particular orexin-1 receptors and orexin-2 receptors. In particular, these compounds are of potential use in the treatment of obesity, including obesity observed in Type 2 (non-insulin-dependent) diabetes patients, gastrointestinal disorders and/or sleep disorders. Additionally these compounds are useful in stroke, particularly ischemic or haemorrhagic stroke, and/or blocking the emetic response i.e. the compounds are useful in the treatment of nausea and vomiting.

International Patent Applications WO99/09024, WO99/58533, WO0/47577 and WO00/47580 disclose phenyl urea derivatives and WO00/47576 discloses quinolinyl cinnamide derivatives as orexin receptor antagonists. WO01/96302 discloses N-aroyl cyclic amine derivatives and WO02/44172 discloses morpholine derivatives as orexin receptor antagonists.

According to the present invention there is provided a compound of formula (I):

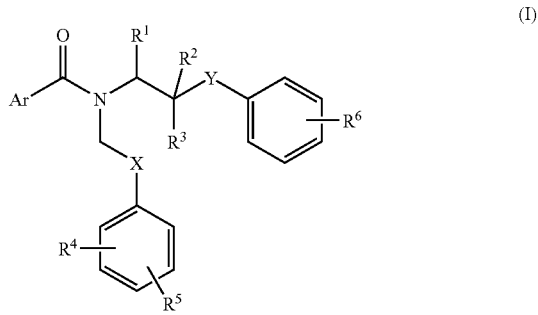

wherein:

$R^1$ is hydrogen;

$R^2$ is $(C_{1-3})$alkyl; and $R^3$ is hydrogen or $(C_{1-3})$alkyl; or $R^2$ and $R^3$ together with the carbon to which they are attached form a $(C_{3-5})$cycloalkcyl group; or $R^1$ is $(C_{1-3})$alkyl; $R^2$ is hydrogen; and $R^3$ is hydrogen, or $(C_{1-3})$alkyl;

$R^4$ and $R^5$ are independently selected from hydrogen, halogen, NC—, optionally substituted $(C_{1-6})$ alkylCO, optionally substituted $(C_{1-6})$alkyl, optionally substituted $(C_{1-6})$ alkoxy, optionally substituted $(C_{1-6})$alkylOCO—, and optionally substituted $(C_{1-6})$alkylNHCO—; provided that $R^4$ and $R^5$ are not both hydrogen;

$R^6$ is hydrogen or halogen;

Ar represents an optionally substituted aryl or an optionally substituted 5- or 6-membered aromatic heterocyclyl group containing up to 3 heteroatoms selected from N, O and S; or Ar represents an optionally substituted bicyclic heteroaryl group containing up to 3 heteroatoms selected from N, O and S;

X is —$CH_2$—, or a bond;

Y is —NHCO—, or a bond;

or a pharmaceutically acceptable derivative thereof.

The group Ar may be optionally substituted by 1 to 5, preferably 1 to 3, substituents.

When Ar is aryl it is suitably phenyl or naphthyl.

Examples of a 5- or 6-membered aromatic heterocyclyl group containing up to 3 heteroatoms selected from N, O and S include furanyl, thienyl, pyrrolyl, oxazolyl, thiazolyl, imidazolyl, oxadiazolyl, thiadiazolyl, triazolyl, triazinyl, pyridazinyl, pyrimidinyl, isothiazolyl, isoxazolyl, pyrazinyl, or pyrazolyl.

When Ar is bicyclic heteroaryl it is, for example, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl or naphthyridinyl.

Preferably Ar represents phenyl, naphthyl, quinolinyl, isoquinolinyl, benzothiazolyl, benzoxadiazolyl, benzothiadiazolyl, thiazolyl, triazolyl, or pyrazolyl, any of which may be optionally substituted.

Optional substituents for Ar include phenyl optionally substituted by halogen; a 5- or 6-membered aromatic heterocyclyl group containing up to 3 heteroatoms selected from N, O and S, optionally substituted by $(C_{1-4})$alkyl; halogen, hydroxy, oxo, cyano, nitro, $(C_{1-4})$alkyl, hydroxy$(C_{1-4})$alkyl, $(C_{1-4})$alkoxy, hydroxy$(C_{1-4})$alkoxy, halo$(C_{1-4})$alkyl, halo$(C_{1-4})$alkoxy, aryl$(C_{1-4})$alkoxy, $(C_{1-4})$alkylthio, hydroxy$(C_{1-4})$alkyl, $(C_{1-4})$alkoxy$(C_{1-4})$alkyl, $(C_{3-6})$cycloalkyl$(C_{1-4})$alkoxy, $(C_{1-4})$alkanoyl, $(C_{1-4})$alkoxycarbonyl, $(C_{1-4})$alkylsulfonyl, $(C_{1-4})$ alkylsulfonyloxy, $(C_{1-4})$alkylsulfonyl$(C_{1-4})$alkyl, arylsulfonyl, arylsulfonyloxy, arylsulfonyl$(C_{1-4})$alkyl, $(C_{1-4})$alkylsulfonamido, $(C_{1-4})$alkylamido, $(C_{1-4})$alkylsulfonamido$(C_{1-4})$alkyl, $(C_{1-4})$alkylamido$(C_{1-4})$alkyl, arylsulfonamido, arylcarboxamido, arylsulfonamido$(C_{1-4})$alkyl, arylcarboxamido$(C_{1-4})$alkyl, aroyl, aroyl$(C_{1-4})$alkyl, or aryl$(C_{1-4})$alkanoyl group; a group $R^xR^yN$—, $R^xOCO(CH_2)_r$, $R^xCON(R^y)(CH_2)_r$, $R^xR^yNCO(CH_2)_r$, $R^xR^yN(CH_2)_rO$, $R^xR^yNSO_2(CH_2)_r$ or $R_xSO_2NR^y(CH_2)_r$ where each of $R^x$ and $R^y$ independently represents a hydrogen atom or a $(C_{1-4})$alkyl group or where appropriate $R^xR^y$ forms part of a $(C_{3-6})$ azacycloalkane or $(C_{3-6})(2$-oxo) azacycloalkane ring and r represents zero or an integer from 1 to 4. Additionally, when Ar is phenyl two substituents on adjacent carbon atoms may, together with the ring to which they are attached, form a bicyclic or tricyclic heterocyclyl or carbocyclyl ring system, for example, fluorenyl, 1,3-benzodioxolyl, or dihydrobenzofuryl, any of which may be optionally substituted by halogen or oxo.

Optional substituents for the groups $R^4$ and $R^5$ include halogen.

Preferred optional substituents for a group Ar include phenyl optionally substituted by halogen; oxadiazolyl substituted by $(C_{1-4})$alkyl; halogen, cyano, $(C_{1-4})$alkyl, $(C_{1-4})$alkoxy, halo$(C_{1-4})$alkyl, halo$(C_{1-4})$alkoxy, $(C_{1-4})$alkoxycarbonyl, $(C_{1-4})$alkylsulfonyl, $(C_{1-4})$alkylamido, $R^xR^yN(CH_2)_rO$, where each of $R^x$ and $R^y$ independently represents a hydrogen atom or a $(C_{1-4})$ alkyl group and r represents zero or an integer from 2 to 4. Additionally, when Ar is phenyl two substituents on adjacent carbon atoms may, together with the ring to which they are attached, form a fluorenyl, 1,3-benzodioxolyl, or dihydrobenzofuryl ring system, any of which may be optionally substituted by halogen or oxo.

More preferably optional substituents for a group Ar are independently selected from: phenyl optionally substituted by halogen e.g. F; oxadiazolyl optionally substituted by methyl; Br, Cl, F, NC—, $CH_3$—, $CF_3$—, $CH_3O$—, $CF_3O$—, $(CH_3)_2NCH_2CH_2O$, $CH_3CONH$—, and $CH_3SO_2$— or, when Ar is phenyl, two substituents on adjacent carbons together with the phenyl ring to which they are attached form a group selected from 9-fluorenon-4-yl, 1,3-benzodioxol-5-yl, and 5-bromodihydrobenzofur-7-yl.

Preferably substituents on the group Ar are ortho and/or meta to the amide linker.

Examples of $R^4$ and $R^5$ are hydrogen, halogen, NC—, optionally substituted $(C_{1-4})$alkoxy, optionally substituted $(C_{1-4})$alkylOCO—, and optionally substituted $(C_{1-4})$alkylCO—.

Further examples of $R^4$ and $R^5$ are hydrogen, halogen, NC—, optionally substituted $(C_{1-4})$ alkoxy, and optionally substituted $(C_{1-4})$alkylCO—.

When $R^1$ is hydrogen, then $R^2$ and $R^3$ are preferably the combinations methyl/hydrogen, ethyl/hydrogen or methyl/methyl.

When $R^2$ is $(C_{1-3})$alkyl and $R^1$ and $R^3$ are hydrogen the R-enantiomer is preferred.

When $R^1$ is $(C_{1-3})$alkyl and $R^2$ and $R^3$ are hydrogen, the S-enantiomer is preferred.

When a halogen atom is present in the compound of formula (I) it may be fluorine, chlorine, bromine or iodine.

A preferred compound is (R)-benzo[1,3]dioxole-5-carboxylic acid [2-(3,4-dimethoxy-phenyl)-ethyl]-(2-phenyl-propyl)-amide or a pharmaceutically acceptable derivative thereof.

A further preferred compound is (R)-2-cyano-N-[2-(3,4-dimethoxy-phenyl)-ethyl]-N-(2-phenyl-propyl)-benzamide) or a pharmaceutically acceptable derivative thereof.

When the compound of formula (I) contains an alkyl group, whether alone or forming part of a larger group, e.g. alkoxy or alkylthio, the alkyl group may be straight chain, branched or cyclic, or combinations thereof, then it is preferably methyl or ethyl.

It will be appreciated that compounds of formula (I) may exist as R or S enantiomers. The present invention includes within its scope all such isomers, including mixtures. Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

It will be understood that the invention includes pharmaceutically acceptable derivatives of compounds of formula (I) and that these are included within the scope of the invention.

Particular compounds according to the invention include those mentioned in the examples and their pharmaceutically acceptable derivatives.

As used herein "pharmaceutically acceptable derivative" includes any pharmaceutically acceptable salt, solvate, ester or salt or solvate of such ester of a compound of formula (I) which, upon administration to the recipient is capable of providing (directly or indirectly) a compound of formula (I) or an active metabolite or residue thereof. Preferred pharmaceutically acceptable derivatives according to the invention are any pharmaceutically acceptable salts and solvates.

It will be appreciated that for use in medicine the salts of the compounds of formula (I) should be pharmaceutically acceptable. Suitable pharmaceutically acceptable salts will be apparent to those skilled in the art and include acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further feature of the invention there is provided a process for the preparation of compounds of formula (I) and salts thereof. The following schemes detail synthetic routes to compounds of the invention.

Compounds of formula (I) may be prepared from convenient starting materials by adapting synthetic procedures well known in the art. Preferably, the final stage involves the formation of an amide bond between a compound of formula (II) and a compound of formula (III):

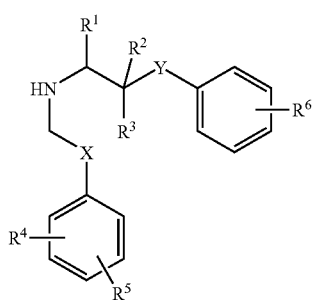

(II)

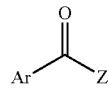

(III)

wherein Ar, $R^1$, $R^2$, $R^3$, $R^4$, $R^5$, $R^6$, X and Y are as hereinbefore defined for compounds of formula (I), and Z is a leaving group or a group converted to a leaving group in-situ followed by, if necessary or so desired, conversion to a pharmaceutically acceptable derivative thereof.

Z is suitably halogen, hydroxy, OC(=O)alkyl or OC(=O)Oalkyl, particularly halogen, for example chloro.

Amide bond forming conditions are well known in the art and include reaction of the amine with an appropriate acid chloride in an inert solvent such as dichloromethane, optionally in the presence of a base such as triethylamine or N,N-diisopropylethylamine. Alternatively, the amine may be coupled directly with an appropriate carboxylic acid using a reagent such as 1-(3-dimethylaminopropyl)-3-ethylcarbodi-imide with 1-hydroxybenzotriazole or O-(7-azabenzotriazol-1-yl)-N,N,N',N'-tetramethyluronium hexafluorophosphate (HATU) with a base such as triethylamine or N,N-diisopropylethylamine.

Compounds of formula (II) and (III) are known in the literature or can be prepared by known methods. A compound of formula (II) may be prepared by reacting a compound of formula (IV) with a compound of formula (V):

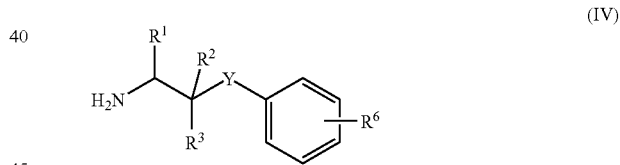

(IV)

(V)

wherein $R^1$, $R^2$, $R^3$, $R^4$, $R^5$, $R^6$, X and Y are as hereinbefore defined, in the presence of a reducing agent. Suitable reducing agents which may be employed include sodium borohydride, sodium cyanoborohydride or sodium triacetoxyborohydride under acidic conditions, or catalytic hydrogenation. The reaction may conveniently be effected in a solvent such as ethanol or dichloroethane.

A compound of formula (II) where $R^1$=H may also be prepared by reaction of a compound of formula (VI) with a compound of formula (VII):

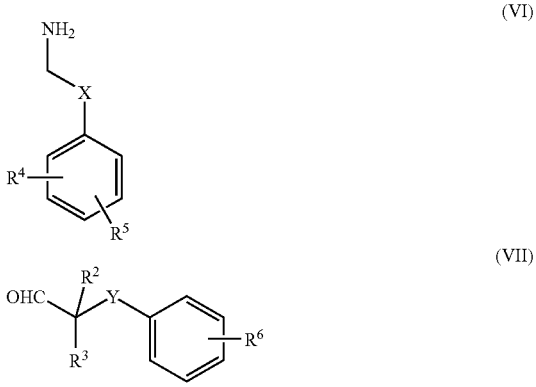

wherein $R^2$, $R^3$, $R^4$, $R^5$, $R^6$, X and Y are as hereinbefore defined for compounds of formula (I), in the presence of a reducing agent. Suitable reducing conditions which may be employed include those defined above for the reaction of a compound of formula (IV) with a compound of formula (V) in the presence of a reducing agent.

A compound of formula (II) may also be prepared from an amide of formula (VIII) or where $R^1$=H, an amide of formula (IX):

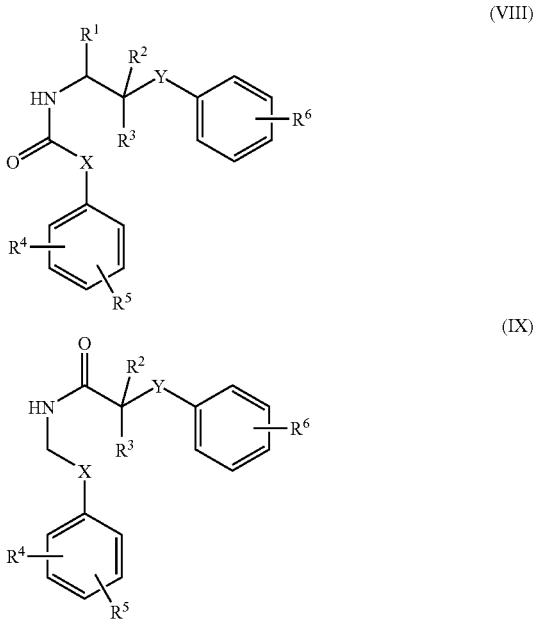

wherein $R^1$, $R^2$, $R^3$, $R^4$, $R^5$, $R^6$, X and Y are as hereinbefore defined for compounds of formula (I), by reduction of the amide carbonyl. Suitable reducing agents include lithium aluminium hydride or diborane in the presence of a solvent such as tetrahydrofuran or diethyl ether.

Intermediates of formulae (III), (IV), (V), (VI), (VIII), (VIII) and (IX) are commercially available, or may be made by known routes from commercially available materials.

Compounds of formula (III) may be prepared according to processes known in the art for the preparation of acyl groups, for example *The Chemistry of Acyl Halides*, S. Patai (Ed), Interscience, New York, 1972.

Amines of formula (IV) and formula (VI) may be made by methods known to the skilled person, for example those described in *The Amino Group*, S. Patai (Ed), Interscience, New York 1968.

Aldehydes of formula (V) or formula (VII) may be made by methods known in the art, for example those described in *The Chemistry of the Carbonyl Group*, S. Patai (Ed), Interscience, New York, 1966.

Amides of formula (VIII) and formula (IX) may be made by known methods such as those described in *The Chemistry of Amides*, J. Zabicky (Ed), Interscience, New York, 1970.

The compounds of formula (I) may be prepared singly or as compound libraries comprising at least 2, e.g. 5 to 1000, preferably 10 to 100 compounds of formula (I). Compound libraries may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

Pharmaceutically acceptable salts may be prepared conventionally by reaction with the appropriate acid or acid derivative.

The compounds of formula (I) and their pharmaceutically acceptable derivatives are useful for the treatment of diseases or disorders where an antagonist of a human orexin receptor is required such as obesity and diabetes; prolactinoma; hypoprolactinemia; hypothalamic disorders of growth hormone deficiency; idiopathic growth hormone deficiency; Cushings syndrome/disease; hypothalamic-adrenal dysfunction; dwarfism; sleep disorders; sleep apnoea; narcolepsy; insomnia; parasomnia; jet-lag syndrome; sleep disturbances associated with diseases such as neurological disorders, neuropathic pain and restless leg syndrome; heart and lung diseases; depression; anxiety; addictions; obsessive compulsive disorder; affective neurosis/disorder; depressive neurosis/disorder; anxiety neurosis; dysthymic disorder; behavior disorder, mood disorder; sexual dysfunction; psychosexual dysfunction; sex disorder; sexual disorder; schizophrenia; manic depression; delerium; dementia; bulimia; ischemic or haemorrhagic stroke and hypopituitarism.

The compounds of formula (I) and their pharmaceutically acceptable derivatives are particularly useful for the treatment of obesity, including obesity associated with Type 2 diabetes, stroke and sleep disorders.

Other diseases or disorders which may be treated in accordance with the invention include disturbed biological and circadian rhythms; adrenohypophysis disease; hypophysis disease; hypophysis tumor/adenoma; adrenohypophysis hypofunction; functional or psychogenic amenorrhea; adrenohypophysis hyperfunction; migraine; hyperalgesia; pain; enhanced or exaggerated sensitivity to pain such as hyperalgesia, causalgia and allodynia; acute pain; burn pain; atypical facial pain; neuropathic pain; back pain; complex regional pain syndromes I and II; arthritic pain; sports injury pain; pain related to infection e.g. HIV, post-polio syndrome and post-herpetic neuralgia; phantom limb pain; labour pain; cancer pain; post-chemotherapy pain; post-stroke pain; post-operative pain; neuralgia; and tolerance to narcotics or withdrawal from narcotics.

The invention also provides a method of treating or preventing diseases or disorders where an antagonist of a human orexin receptor is required, which comprises administering to a subject in need thereof an effective amount of a compound of formula (I), or a pharmaceutically acceptable derivative thereof.

The invention also provides a compound of formula (I), or a pharmaceutically acceptable derivative thereof, for use in the treatment or prophylaxis of diseases or disorders where an antagonist of a human orexin receptor is required.

The invention also provides the use of a compound of formula (I), or a pharmaceutically acceptable derivative thereof, in the manufacture of a medicament for the treatment or prophylaxis of diseases or disorders where an antagonist of a human orexin receptor is required.

For use in therapy the compounds of the invention are usually administered as a pharmaceutical composition. The invention also provides a pharmaceutical composition comprising a compound of formula (I), or a pharmaceutically acceptable derivative thereof, and a pharmaceutically acceptable carrier.

The compounds of formula (I) and their pharmaceutically acceptable derivatives may be administered by any convenient method, e.g. by oral, parenteral, buccal, sublingual, nasal, rectal or transdermal administration, and the pharmaceutical compositions adapted accordingly.

The compounds of formula (I) and their pharmaceutically acceptable derivatives which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluoro-chlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I), or a pharmaceutically acceptable derivative thereof, used in the treatment or prophylaxis of the abovementioned disorders or diseases will vary in the usual way with the particular disorder or disease being treated, the weight of the subject and other similar factors. However, as a general rule, suitable unit doses may be 0.05 to 1000 mg, more suitably 0.05 to 500 mg. Unit doses may be administered more than once a day for example two or three times a day, so that the total daily dosage is in the range of about 0.01 to 100 mg/kg; and such therapy may extend for a number of weeks or months. In the case of pharmaceutically acceptable derivatives the above figures are calculated as the parent compound of formula (I).

No toxicological effects are indicated/expected when a compound of formula (I) is administered in the above mentioned dosage range.

Human orexin-A has the amino acid sequence:

```
pyroGlu Pro Leu Pro Asp Cys Cys Arg Gln Lys Thr Cys Ser Cys Arg Leu
   1           5              10                 15

Tyr Glu Leu Leu His Gly Ala Gly Asn His Ala Ala Gly Ile Leu Thr
           20               25                30

Leu-NH₂
```

Orexin-A can be employed in screening procedures for compounds which inhibit the ligand's activation of the orexin-1 receptor.

In general, such screening procedures involve providing appropriate cells which express the orexin-1 receptor on their surface. Such cells include cells from mammals, yeast, *Drosophila* or *E. coli*. In particular, a polynucleotide encoding the orexin-1 receptor is used to transfect cells to express the receptor. The expressed receptor is then contacted with a test compound and an orexin-1 receptor ligand to observe inhibition of a functional response. One such screening procedure involves the use of melanophores which are transfected to express the orexin-1 receptor, as described in WO 92/01810.

Another screening procedure involves introducing RNA encoding the orexin-1 receptor into *Xenopus* oocytes to transiently express the receptor. The receptor oocytes are then contacted with a receptor ligand and a test compound, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on their surface. This method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand may contain a radioactive label. The amount of labelled ligand bound to the receptors is measured, e.g. by measuring radioactivity.

Yet another screening technique involves the use of FLIPR equipment for high throughput screening of test compounds that inhibit mobilisation of intracellular calcium ions, or other ions, by affecting the interaction of an orexin-1 receptor ligand with the orexin-1 receptor.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention. The Descriptions illustrate the preparation of intermediates to compounds of the invention.

Abbreviations used herein are as follows: MDC is dichloromethane, THF is tetrahydrofuran, DMF is N,N-dimethylformamide and TFA is trifluoroacetic acid, EtOAc is ethyl acetate and DMSO is dimethyl sulphoxide.

The following Examples illustrate the preparation of pharmacologically active compounds of the invention. The Descriptions D1-D22 illustrate the preparation of intermediates to compounds of the invention. $^1$H NMR's were measured at 250 MHz in CDCl$_3$ unless otherwise stated.

DESCRIPTION 1a (R,S)-(3-Bromo-methoxy-benzyl)-(2-phenylpropyl)-amine

A solution of 3-bromo-4-methoxy-benzaldehyde (2.15 g, 10 mmol) and (R,S)-1-amino-2-phenylpropane (1.35 g, 10 mmol) in 1,2-dichloroethane (50 ml) was stirred at room temperature under argon for 0.5 h. Sodium triacetoxyborohydride (2.97 g, 14 mmol) was added over 5 min. then stirring was continued for a further 16 h. The reaction mixture was diluted with MDC (50 ml) and then washed with saturated aqueous K$_2$CO$_3$. The aqueous phase was extracted with MDC and the combined organics then washed with brine. The organic phase was dried (MgSO$_4$) and the solvent removed in vacuo. The residue was chromatographed (silica gel, 20–50% EtOAc-pentane) to afford the title compound as a colourless oil (1.90 g, 57%).

MS (API$^+$): Found MH$^+$334. C$_{17}$H$_{20}$$^{79}$BrNO requires 333.

$^1$H NMR δ: 1.25 (3H, d, J=7 Hz), 2.75 (2H, d, J=7 Hz), 2.96 (1H, m), 3.65 (2H, m), 3.88 (3H, s), 6.82 (1H, d, J=8 Hz), 7.05–7.36 (6H, m), 7.42 (111, d, J=2 Hz).

The following compounds were prepared in a similar manner to Description 1a

DESCRIPTION 1b (R,S)-(3,4-Dimethoxy-benzyl)-(2-phenyl-propyl)-amine

MS (API$^+$): Found MH$^+$286. C$_{18}$H$_{23}$NO$_2$ requires 285.
$^1$H NMR δ: 1.25 (3H, d, J=7 Hz), 2.77 (2H, d, J=7 Hz), 2.96 (1H, m), 3.69 (2H, m), 3.84 (3H, s), 3.86 (3H, s), 6.77 (3H, m), 7.23–7.35 (5H, m).

DESCRIPTION 1c (R)(3,4-Dimethoxy-benzyl)-(2-phenylpropyl)-amine

MS (API$^+$): Found MH$^+$286. C$_{18}$H$_{23}$NO$_2$ requires 285.

DESCRIPTION 1d (R,S)-(3-Bromo methoxy-benzyl)-2-phenyl-butyl)-amine

Prepared from 2-phenylbutylamine (Maryanoff et al, *J. Org. Chem.*, 1341,51(8),1986).
MS (API$^+$): Found MH$^+$348. C$_{18}$H$_{22}$$^{79}$BrNO requires 347.
$^1$HNMR δ: 0.78 (3H, t, J=7 Hz), 1.42–1.80 (2H, m), 2.62–2.88 (3H, m), 3.64 (2H, m), 3.87 (3H, s), 6.81 (1H, d, J=8 Hz), 7.05–7.36 (6H, m), 7.40 (1H, d, J=2 Hz).

DESCRIPTION 1e (R,S-(3-Ethoxy-4-methoxy-benzyl)-(2-phenyl-propyl)-amine

MS (API$^+$): Found MH$^+$300. C$_{19}$H$_{25}$NO$_2$ requires 299.
$^1$H NMR δ: 1.18 (3H, d, J=7 Hz), 1.45 (3H, t, J=7 Hz), 2.77 (2H, d, J=7 Hz), 2.96 (1H, m), 3.69 (2H, AB q), 3.85 (311, s), 4.05 (2H, q, J=7 Hz), 6.75 (3H, m), 7.25 (5H, m).

DESCRIPTION 1f (R,S)-[2-(3,4-Dimethoxy-phenyl)-ethyl]-(2-phenyl-propyl)amine

Prepared form 2-phenyl-propionaldehyde and 2-(3,4-dimethoxyphenyl)-ethylamine.
MS (API$^+$): Found MH$^+$300. C$_{19}$H$_{25}$NO$_2$ requires 299.
$^1$H NMR δ: 1.24 (3H, d, J=7 Hz), 2.65–2.93 (7H, bm), 3.82 (3H, s), 3.85 (3H, s), 6.64 (2H, m), 6.74 (1H, d, J=8 Hz), 7.15 (3H, m), 7.25 (2H, m).

DESCRIPTION 1g (R,S)-2-Methoxy-5[(2-phenyl-propylamino)-methyl]-benzoic acid methyl ester $^1$H NMR δ: 1.26 (3H, d, J=7 Hz), 2.76 (2H, d, J=7 Hz), 2.94 (1H, m), 3.70 (2H, AB q), 3.89 (6H, s), 6.91 (1H, d, J=9 Hz), 7.15–7.40 (6H, m), 7.66 (1H, d, J=2 Hz).

DESCRIPTION 2

N-(3,4-Dimethoxy-benzyl)$_2$-phenyl-isobutyramide

A solution of 2-methyl-2-phenylpropionic acid (3.28 g, 20 mmol) in DMF (50 ml) was treated sequentially with N,N-diisopropylethylamine (8.09 g, 80 mmol), O-(7-azabenzotriazol-1-yl)-N,N,N',N'-tetramethyluronium hexafluorophosphate (HATU) (7.60 g, 20 mmol) then 3,4-dimethoxybenzylamine (3.34 g, 20 mmol) and then stirred at room temperature, under argon for 24 h. The reaction mixture was diluted with EtOAc then washed with water (3×) then brine. The organic phase was dried (MgSO$_4$) and the solvent removed in vacuo. The residue was triturated with diethyl ether/pentane to afford the title compound as a beige solid (5.95 g, 95%).

MS (API$^+$): Found MH$^+$314. C$_{19}$H$_{23}$NO$_3$ requires 313.

$^1$H NM δ: 1.60 (6H, s), 3.80 (3H, s), 3.84 (3H, s), 4.32 (2H, d, J=6 Hz), 5.44 (1H, bs), 6.65 (2H, m), 6.76 (1H, d, J=8 Hz), 7.20–7.44 (5H, m).

DESCRIPTION 3

(3,4-Dimethoxy-benzyl(2-methyl-2-phenyl-propyl)amine

A solution of N-3,4-dimethoxybenzyl)$_2$-phenyl-isobutyramide (D2, 4.00 g, 12.8 mmol) in THF (30 ml) was added drop-wise to an ice-cooled solution of lithium aluminium hydride (25.6 mmol) in THF (75 ml) under argon. The reaction mixture was stirred at room temperature for 1 h then at reflux for 8 h. The reaction mixture was ice-cooled then treated with aqueous THF until effervescence ceased and then aqueous 40% NaOH (2 ml) added. After stirring for a further 0.5 h the mixture was filtered through kieselguhr, washing with diethyl ether. The filtrate was washed with brine, dried (MgSO$_4$) and the solvent removed in vacuo. The residue was dissolved in EtOAc and washed with 0.5N HCl. The aqueous phase was basified with aqueous K$_2$CO$_3$ then extracted with EtOAc (2×). The combined organics were dried (MgSO$_4$) and the solvent was removed in vacuo to give the title compound as a colourless oil (1.23 g, 32%).

MS (API$^+$): Found MH$^+$300. C$_{19}$H$_{25}$NO$_2$ requires 299.

$^1$H NMR δ: 1.35 (6H, s), 2.69 (2H, s), 3.66 (2H, s), 3.83 (3H, s), 3.87 (3H, s), 6.75 (3H, m), 7.14-7.38 (5H, m).

DESCRIPTION 4

3-Bromo-methoxybenzylamine

A stirring solution of 3-bromo-4-methoxy-benzonitrile (1.00 g, 4.7 mmol) in THF (30 ml) was treated drop-wise with borane-THF (14.2 ml, 1M solution in THF, 14.2 mmol). The mixture was heated at reflux, under argon for 5 h. To the cooled reaction mixture was cautiously added MeOH (20 ml). The volatiles were removed in vacuo and the residue was treated with 2N HCl (20 ml). After heating at reflux for 0.45 h and cooling to room temperature the mixture was basified by addition of solid K$_2$CO$_3$. The basic solution was extracted with diethyl ether (2×). The organic phase was dried (MgSO$_4$) and the solvent removed in vacuo to afford the title compound as a colourless oil (64%).

$^1$H NMR δ: 1.48 (2H, bs), 3.79 (2H, s), 3.88 (3H, s), 6.86 (1H, d, J=8.4 Hz), 7.21 (1H, dd, J=2 and 8 Hz), 7.51 (1H, d, J=2 Hz)

DESCRIPTION 5

N-3-Bromo-4-methoxy-benzyl)-2-phenyl-isobutyramide

A solution of 2-methyl-2-phenylpropionic acid (1.51 g, 9.2 mmol) in DME (30 ml) was treated sequentially with 1-(3-dimethylamionopropyl)-3-ethylcarbodiimide hydrochloride (1.76 g, 9.2 mmol), 3-bromo-4-methoxybenzylamine (D4, 2.00 g, 9.3 mmol) then 1-hydroxybenzotriazole (0.20 g). After stirring at room temperature, under argon for 16 h the reaction mixture was diluted with EtOAc and washed with water (2×) then brine. The organic phase was dried (MgSO$_4$) and the solvent removed in vacuo. The residue was triturated with diethyl ether/pentane to afford the title compound as an off-white solid (2.3 g, 70%).

MS (API$^+$): Found MH$^+$362. C$_{18}$H$_{20}$$^{79}$BrNO requires 361.

$^1$H NMR δ: 1.60 (6H, s), 3.86 (3H, s), 4.28 (2H, d, J=6 Hz), 5.44 (1H, bm), 6.79 (1H, d, J=8 Hz), 7.05 (1H, dd, J=2, 8 Hz), 7.26 (2H, m), 7.36 (4H, m).

DESCRIPTION 6

(3-Bromo-4-methoxy-benzyl)-(2-methyl-2-phenyl-propyl)amine

A stirring solution of N-3-bromo-4-methoxybenzyl-2-phenyl-isobutyramide (D5, 2.30 g, 6.4 mmol) in THF (50 ml) was treated dropwise with borane-THF (12.8 ml, 1M solution in THF, 12.8 mmol). The mixture was heated at reflux, under argon for 3.5 h. To the cooled reaction mixture was cautiously added MeOH (35 ml). The volatiles were removed in vacuo and the residue was treated with 2N HCl (70 ml). After heating at reflux for 0.5 h and cooling to room temperature the mixture was basified by addition of NaOH pellets. The basic solution was extracted with MDC (2×). The organic phase was dried (MgSO$_4$) and the solvent removed in vacuo. The residue was chromatographed (silica gel, 0–7.5% MeOH-MDC) to afford the title compound as a colourless oil (1.92 g, 86%).

MS (API$^+$): Found MH$^+$348. C$_{18}$H$_{22}$$^{79}$BrNO requires 347.

$^1$H NMR δ: 1.34 (6H, s), 2.67 (2H, s), 3.62 (2H, s), 3.87 (3H, s), 6.81 (1H, d, J=8 Hz), 7.10 (1H, dd, J=2, 8 Hz), 7.20 (1H, m), 7.32 (4H, m), 7.39 (1H, d, J=2 Hz).

DESCRIPTION 7

(S)-(3,4-Dimethoxy-benzyl)-(1-methyl-2-phenyl-ethyl)-amine

A solution of 3,4-dimethoxybenzaldehyde (1.06 g, 6.4 mmol), (S)-1-methyl-2-phenylethylamine sulfate (1.18 g, 6.4 mmol) and triethylamine (0.89 ml, 6.4 mmol) in 1,2-dichloroethane (50 ml) was stirred at room temperature under argon for 15 min. Sodium triacetoxyborohydride (2.97 g, 14 mmol) was added over 5 min. then stirring was continued for a further 16 h. The reaction mixture was diluted with MDC (50 ml) then washed with saturated aqueous K$_2$CO$_3$. The aqueous phase was extracted with MDC and the combined organics washed with brine. The organic phase was dried (MgSO$_4$) and the solvent removed in vacuo. The residue was chromatographed (silica gel, 0–100% EtOAc-pentane) to afford the title compound as a colourless oil (1.20 g, 67%).

MS (API$^+$): Found MH$^+$286. C$_{18}$H$_{23}$NO$_2$ requires 285.

$^1$H NMR δ: 1.10 (3H, d, J=6 Hz), 2.70 (2H, m), 2.91 (1H, m), 3.70 (2H, m), 3.82 (3H, s), 3.86 (3H, s), 2.75 (3H, m), 7.20 (5H, m).

DESCRIPTION 8

(S)-[2-(3,4-Dimethoxy-phenyl)-ethyl]-(1-methyl-2-phenyl-ethyl)-amine

The title compound was prepared from (3,4-dimethoxyphenyl)acetaldehyde (Kraus et al, *J. Org. Chem.*, 1720, 64, 1999) according to a procedure similar to that for Description 7.

MS (API$^+$): Found MH$^+$300. $C_{19}H_{25}NO_2$ requires 299.

$^1$H NMR δ: 1.07 (3H, d, J=6 Hz), 2.55–3.00 (7H, m), 3.84 (3H, s), 3.96 (3H, s), 6.70 (3H, m), 7.10 (2H, m), 7.25 (3H, m).

DESCRIPTION 9

(R,S)-[2-(4-chloro-phenyl)-propyl]-(3,4,dimethoxy-benzyl)amine

The title compound was prepared from 2-(4-chloro-phenyl)-propylamine hydrochloride according to a procedure similar to that for Description 7.

MS (API$^+$): Found MH$^+$320. $C_{18}H_{22}{}^{35}ClNO_2$ requires 319.

$^1$H NMR δ: 1.23 (3H, d, J=7 Hz), 2.80 (2H, m), 3.00 (1H, m), 3.75 (2H, AB q), 3.84 (3H, s), 3.86 (3H, s), 5.60 (1H, bs), 6.78 (3H, m), 7.10 (2H, m), 7.25 (21H, m)

DESCRIPTION 10

(R,S)-2-Methoxy-[(2-phenyl-propylamino)-methyl]-N-propyl benzamide

A solution of (R,S-2-methoxy-5-[(2-phenyl-propylamino)-methyl]-benzoic acid methyl ester (D1g, 1.16 g, 3.7 mmol) in n-propylamine (5 ml) was allowed to stand at room temperature for 12 days. Removal of the volatiles in vacuo afforded the title compound (1.26 g, 100%).

$^1$H NMR δ: 0.96 (3H, t, J=7 Hz), 1.24 (3H, d, J=7 Hz), 1.60 (2H, m), 2.76 (2H, dd, J=1, 7 Hz), 2.96 (1H, m), 3.42 (2H, m), 3.73 (2H, s), 3.94 (3H, s), 6.91 (1H, d, J=8 Hz), 7.15–7.40 (6H, bm), 7.87 (1H, bt), 8.06 (1H, d, J=2 Hz).

DESCRIPTION 11

(R)-2-(3,4-Dimethoxy-phenyl)-N-(2-phenylpropyl)-acetamide

The title compound was prepared from (R)-1-amino-2-phenylpropane according to a procedure similar to that for Description 2.

MS (API$^+$): Found MH$^+$314. $C_{19}H_{23}NO_3$ requires 313.

$^1$H NMR δ: 1.20 (3H, d, J=7 Hz), 2.80 (1H, m), 3.15 (1H, m), 3.43 (2H, s), 3.60 (1H, in), 3.80 (3H, s), 3.88 (3H, s), 5.23 (1H, bt), 6.60 (2H, m), 6.75 (1H, d, J=8 Hz), 7.06 (2H, m), 7.20 (3H, m).

DESCRIPTION 12

(R)-[2-(3,4-Dimethoxy-phenyl)-ethyl]-2-phenyl-propyl)-amine

The title compound was prepared from (R)-2-(3,4-dimethoxy-phenyl)-N-(2-phenyl-propyl)-acetamide, D11 according to a procedure similar to that for Description 6.

MS (API$^+$): Found MH$^+$300. $C_{19}H_{25}NO_2$ requires 299.

$^1$H NMR δ: 1.24 (3H, d, J=7 Hz), 2.60–3.05 (7H, bm), 3.83 (3H, s), 3.85 (3H, s), 6.65 (2H, m), 6.74 (1H, d, J=9 Hz), 7.10–7.35 (5H, m).

DESCRIPTION 13

(R,S)-2-Amino-propyl)-carbamic acid tert-butyl ester

A solution of di-tert-butyl dicarbonate (13.9 g, 0.064 mol) in 1,4-dioxane (100 ml) was added dropwise to a stirring solution of (R,S)-propane-1,2-diamine (37.4 g, 0.51 mmol) in 1,4-dioxane (200 ml). After stirring at room temperature, under argon for 16 h the volatiles were removed in vacuo. The residue was dissolved in water and the resulting solution extracted with MDC (3×). The combined organics were dried (MgSO$_4$) and the solvent removed iii vacuo to afford the title compound as a yellow oil (11.1 g, 100%).

MS (API$^+$): Found MH$^+$175. $C_8H_{18}N_2O_2$ requires 174.

$^1$H NMR δ: 1.07 (3H, d, J=6 Hz), 1.29 (2H,bs), 1.44 (94, s), 2.80–3.20 (3H, bm), 5.56 (1H,bt).

DESCRIPTION 14

(R,S){2-[(1-Phenyl-methanoyl)-amino]-propyl}-carbamic acid tert-butyl ester

A solution of (R,S)-(2-amino-propyl)carbamic acid tert-butyl ester (D13, 1.00 g. 5.75 mmol) in MDC (30 ml) was treated with triethylamine (0.88 ml, 6.32 mmol) then benzoyl chloride (0.74 ml, 6.32 mmol). After stirring at room temperature, under argon for 16 h the reaction mixture was washed with saturated, aqueous NaHCO$_3$ then brine. The organic phase was dried (MgSO$_4$) and the solvent removed iii vacuo. The residue was triturated with diethyl ether to afford the title compound as a white solid (1.15 g, 72%).

MS (API$^+$): Found MH$^+$279. $C_{15}H_{22}N_2O_3$ requires 278.

$^1$HNMR δ:1.26 (3H, d, J=7 Hz), 1.40 (9H, s), 3.12–3.52 (2H, m), 4.20 (1H, m), 5.00 (1H, bt), 7.10 (1H, bd), 7.45 (3H, m), 7.82 (2H, m).

DESCRIPTION 15

(R,S)-N-(2-Amino-1-methyl-ethyl)-benzamide

A stirring, ice-cooled solution of (R,S){2-[(1-phenyl-methanoyl)-amino]-propyl}-carbamic acid tert-butyl ester (D14, 1.15 g, 4.14 mmol) in MDC (45 ml) was treated with TFA (5 ml). After 5 min. the ice bath was removed and the reaction mixture was stirred at room temperature, under argon for 2.5 h. The reaction mixture was basified by cautious addition to a minimum of saturated aqueous K$_2$CO$_3$. The aqueous layer was extracted with MDC (2×) then MDC/10% MeOH (2×). The combined organics were dried (MgSO$_4$) and the solvent removed in vacuo to afford the title compound as a colourless gum (0.37 g, 50%). The aqueous extracts were evaporated to dryness and chromatographed (silica gel, 85:14.9:0.1 MDC:MeOH:anmionia) to afford a further batch of the title compound as a sticky white solid (0.28 g, 38%).

MS (API$^+$): Found MH$^+$179. $C_{10}H_{14}N_2O$ requires 178.

DESCRIPTION 16

(R,S)-N-[2-(3,4-Dimethoxy-benzylamino)-1-methyl-ethyl]-benzamide

A solution of 3,4-dimethoxy-benzaldehyde (1.97 g, 1.2 mmol) and (R,S)-N-(2-amino-1-methylethyl)-benzamide (D15, 2.11 g, 1.2 mmol) in 1,2-dichloroethane (60 ml) was stirred at room temperature under argon for 0.5 h. Sodium triacetoxyborohydride (3.77 g, 1.8 mmol) was added over 5 min. then stirring was continued for a further 16 h. The reaction mixture was diluted with MDC (50 ml) and then washed with saturated aqueous $K_2CO_3$. The organic phase was dried ($MgSO_4$) and the solvent removed in vacuo. The residue was chromatographed (silica gel, 0–20% MeOH-EtOAc) to afford the title compound as a colourless gum.

MS ($API^+$): Found $MH^+$329. $C_{19}H_{24}N_2O_3$ requires 328.
$^1$H NMR δ: 1.27 (3H, d, J=7 Hz), 2.77 (2H, d, J=5 Hz), 3.76 (2H, s), 3.82 (3H, s), 3.86 (3H, s), 4.30 (1H, s), 6.64 (1H, bs), 6.55 (3H, m), 7.45 (3H, m), 7.76 (2H, m).

DESCRIPTION 17

(R,S)-N-{2-[2-(3,4-Dimethoxy-phenyl)-ethylamino]-1-methyl-ethyl}-benzamide

The title compound was prepared from (3,4-dimethoxyphenyl)acetaldehyde (Kraus et al, J. Org. Chem., 1720,64, 1999) according to a procedure similar to that for Description 16

MS ($API^+$): Found $MH^+$343. $C_{20}H_{26}N_2O_3$ requires 342.

DESCRIPTION 18

(R,S)-N-(3,4-Dimethoxy-benzyl)-2-(4-fluoro-phenyl)-propionamide

The title compound was prepared from 2-(4-fluoro-phenyl)propionic acid and 3,4-dimethoxybenzylamine according to a procedure similar to that for Description 2. Diethyl ether rather than EtOAc was used as the work-up solvent and the product was purified by trituration with diethyl ether.

MS ($API^+$): Found $MH^+$318. $C_{18}H_{20}FNO_3$ requires 317.
$^1$HNMR δ: 1.53 (3H, d, J=7 Hz), 3.55 (1H, q, J=7 Hz), 3.78 (31, s), 3.85 (3H, s), 4.33 (2H, m), 5.60 (1H, bs), 6.65–6.79 (3H, m), 6.97–7.06 (2H, m), 7.24–7.31 (2H, m).

DESCRIPTION 19

(R,S)-(3,4-Dimethoxy-benzyl)-[2-(4-fluoro-phenyl)-propyl]-amine

The title compound was prepared from (R,S)-N-(3,4-dimethoxy-benzyl-2-(4-fluoro-phenyl)-propionamide, D18 according to a procedure similar to that for Description 6.

$^1$H NMR δ: 1.23 (3H, d, J=7 Hz), 2.68–2.81 (2H, m), 2.93 (1H, m), 3.69 (2H, AB q), 3.85 (3H, s), 3.86 (3H, s), 6.73–6.87 (3H, m), 6.95–7.03 (2H, m), 7.12–7.20 (2H, m).

DESCRIPTION 20

(R,S)-2-Methoxy-5[(2-phenyl-propylamino)methyl]-benzonitrile

A solution of (R,S)-3-bromo-4-methoxy-benzyl)(2-phenyl-propyl)amine (D1a, 2.18 g, 6.53 mmol) and copper (1) cyanide (1.16 g, 13.1 mmol) in 1-methyl-2-pyrrolidinone (75 ml) was heated at reflux, under argon for 5 h. The cooled reaction mixture was filtered through kieselguhr, washing with EtOAc and water. The organic phase was separated and washed with water (2×) then brine (2×), dried ($MgSO_4$) and the solvent removed in vacuo. The residue was chromatographed (silica gel, 0–100% EtOAc-pentane) to afford the title compound as a brown gum (0.23 g, 12%).

MS ($API^+$): Found $MH^+$281. $C_{18}H_{20}N_2O$ requires 280.
$^1$H NMR δ: 1.26 (3H, d, J=7 Hz), 2.74 (2H, d, J=7 Hz), 2.93 (1H, m), 3.68 (2H, s), 3.90 (3H, s), 6.88 (1H, dd, J=1 and 9 Hz), 7.18–7.42 (7H, m).

DESCRIPTION 21

(R,S)-1-{2-Methoxy-5-[(2-phenyl-propylamino)-methyl]-phenyl}-ethanone

A mixture of (R,S)-(3-bromo-4-methoxy-benzyl)(2-phenyl-propyl)-amine (D1a, 1.50 g, 4.50 mmol), tributyl(1-ethoxyvinyl)tin (1.81 ml, 5.36 mmol) and tetrakis(triphenylphosphine)palladium(0) (0.26 g, 0.22 mmol) in 1,4-dioxane (20 ml) was heated at 100° C. for 16 h. The cooled reaction mixture was treated with 2N HCl (5 ml) and the mixture stirred at room temperature for 1.5 h. The reaction mixture was diluted with water and extracted with EtOAc (3×). The combined organics were dried ($MgSO_4$) and the solvent removed in vacuo. The residue was chromatographed (silica gel, 0–10% methanol-EtOAc) to afford the title compound as a yellow gum (0.81 g, 61%).

MS ($API^+$): Found $MH^+$298. $C_{19}H_{23}NO_2$ requires 297.
$^1$H NMR δ: 1.36 (3H, d, J=7 Hz), 2.58 (3H, s), 2.83–2.97 (2H, m), 3.29 (1H, m), 3.87 (2H, s), 3.89 (3H, s), 6.97 (1H, d, J=9 Hz), 7.19–7.40 (5H, m), 7.62 (1H, d, j=2 Hz), 7.70 (1H dd, J=2 and 9 Hz).

DESCRIPTION 22

(S)-(3,4-Dimethoxy-benzyl)-(2-phenyl-propyl)amine

The title compound was prepared from $(S)_2$-amino-phenylpropane according to a procedure similar to that for Description 1a.

MS ($API^+$): Found $MH^+$286. $C_{18}H_{23}NO_2$ requires 285.

The compounds of Examples 1–69 below were prepared from the appropriate amine and acid chloride using a procedure similar to Method A or Method B.

METHOD A

To a solution of the appropriate acid chloride (0.05 mmol) in MDC (0.5 ml) was added the appropriate amine (0.10 mmol) in MDC (0.5 ml) and MDC (0.3 ml). The reaction was allowed to mix for 16 h. Excess Amberlite IRA-93, Trisamine resin and Pol-isocyanate were added and allowed to mix for 16 h. The mixture was filtered through a pre-packed SCX resin column (250 mg). The solvent was evaporated to afford the desired amide which was analysed by LC-MS (>80% purity). The chemistry was carried out in 96 well Robbins Flex Chem Filtration Blocks enabling analogues to be prepared as components of a combinatorial array. Stock solutions of reagents were prepared which were dispensed using Eppendorf pipettes.

METHOD B

To a solution of triethylamine (0.036 mmol) in MDC (0.50 ml) was added a solution of the appropriate amine (0.03 mmol) in MDC (0.25 ml) then the appropriate acid chloride (0.036 mmol) in MDC (0.25 ml). The reaction was allowed to mix for 16 h. Excess Amberlite IRA-93, Trisamine resin and Pol-isocyanate were added and allowed to mix for 18 h. Scavenger resins were filtered, solvent removed and the residue was treated with another portion of excess Amberlite IRA-93 for 4 h. The resin was removed by filtration and the solvent evaporated to give the desired amide which was analysed by LC/MS (>80% purity). The chemistry was carried out in 96 well Robbins Flex Chem Filtration Blocks enabling analogues to be prepared as components of a combinatorial array. Stock solutions of reagents were prepared which were dispensed to the 96 wells simultaneously or to individual wells, as required using either Hydra 96 or Eppendorf pipettes.

TABLE 1

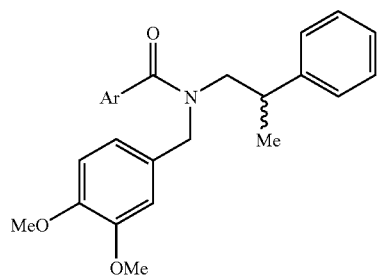

| Example | Method | Ar | MS |
|---|---|---|---|
| 1 | A | —Ph | Found MH+ 390<br>$C_{25}H_{27}NO_3$ requires 389 |
| 2 | A | 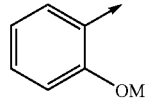 (2-OMe phenyl) | Found MH+ 420<br>$C_{26}H_{29}NO_4$ requires 419 |
| 3 | A | 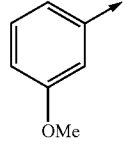 (3-OMe phenyl) | Found MH+ 420<br>$C_{26}H_{29}NO_4$ requires 419 |
| 4 | A | 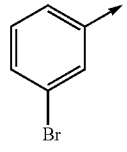 (3-Br phenyl) | Found MH+ 470<br>$C_{25}H_{26}{}^{81}BrNO_3$ requires 469 |
| 5 | A | 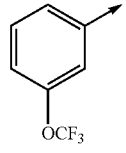 (3-OCF3 phenyl) | Found MH+ 474<br>$C_{26}H_{26}F_3NO_4$ requires 473 |
| 6 | A | 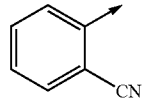 (2-CN phenyl) | Found MH+ 415<br>$C_{26}H_{26}N_2O_3$ requires 414 |

TABLE 1-continued

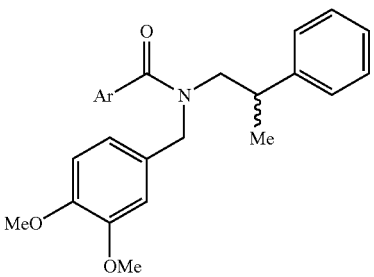

| Example | Method | Ar | MS |
|---|---|---|---|
| 7 | A | 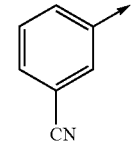 (3-CN phenyl) | Found MH+ 415<br>$C_{26}H_{26}N_2O_3$ requires 414 |
| 8 | A | 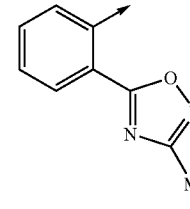 (2-(3-methyl-1,2,4-oxadiazol-5-yl)phenyl) | Found MH+ 472<br>$C_{28}H_{29}N_3O_4$ requires 471 |
| 9 | A | 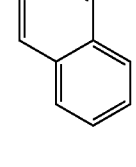 (1-naphthyl) | Found MH+ 440<br>$C_{29}H_{29}NO_3$ requires 439 |
| 10 | A | 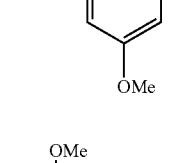 (3,5-diOMe phenyl) | Found MH+ 450<br>$C_{27}H_{31}NO_5$ requires 449 |
| 11 | A | 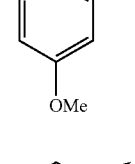 (2,4-diOMe phenyl) | Found MH+ 450<br>$C_{27}H_{31}NO_5$ requires 449 |
| 12 | A | 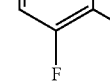 (2,3-diF phenyl) | Found MH+ 426<br>$C_{25}H_{25}F_3NO_3$ requires 425 |

TABLE 1-continued

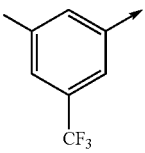

| Example | Method | Ar | MS |
|---|---|---|---|
| 13 | B | 3,5-bis(CF$_3$)-phenyl | Found MH$^+$ 526<br>C$_{27}$H$_{25}$F$_6$NO$_3$ requires 525 |
| 14 | B | 3-F-phenyl | Found MH$^+$ 408<br>C$_{25}$H$_{26}$FNO$_3$ requires 407 |
| 15 | B | 3,4-dichlorophenyl | Found MH$^+$ 458<br>C$_{25}$H$_{25}$$^{35}$Cl$_2$NO$_3$ requires 457 |
| 16 | B | 2,3-dichlorophenyl | Found MH$^+$ 458<br>C$_{25}$H$_{25}$$^{35}$Cl$_2$NO$_3$ requires 457 |

TABLE 1-continued

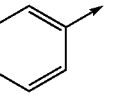

| Example | Method | Ar | MS |
|---|---|---|---|
| 17 | B | 1,3-benzodioxol-5-yl | Found MH$^+$ 434<br>C$_{26}$H$_{27}$NO$_5$ requires 433 |
| 18 | B | 9-oxofluorenyl | Found MH$^+$ 492<br>C$_{32}$H$_{29}$NO$_4$ requires 491 |
| 19 | B | 2-naphthyl | Found MH$^+$ 440<br>C$_{29}$H$_{29}$NO$_3$ requires 439 |
| 20 | B | 4-bromo-2-methoxyphenyl | Found MH$^+$ 498<br>C$_{26}$H$_{28}$$^{79}$BrNO$_4$ requires 497 |

TABLE 2

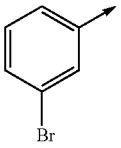

| Example | Method | Ar | MS |
|---|---|---|---|
| 21 | A | 3-bromophenyl | Found MH$^+$ 468<br>C$_{25}$H$_{26}$$^{79}$BrNO$_3$ requires 467 |

TABLE 2-continued
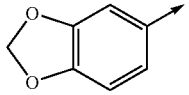
| Example | Method | Ar | MS |
|---|---|---|---|
| 22 | A | 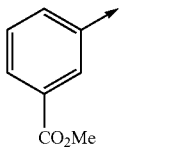 | Found MH⁺ 434<br>$C_{26}H_{27}NO_5$ requires 433 |
| 23 | A | 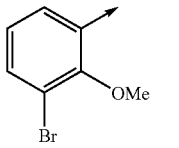 | Found MH⁺ 448<br>$C_{27}H_{29}NO_5$ requires 447 |
| 24 | A | 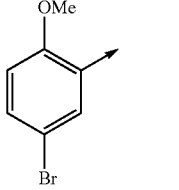 | Found MH⁺ 498<br>$C_{26}H_{28}{}^{79}BrNO_4$ requires 497 |
| 25 | A | 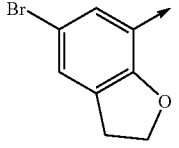 | Found MH⁺ 500<br>$C_{26}H_{28}{}^{81}BrNO_4$ requires 499 |
| 26 | A | 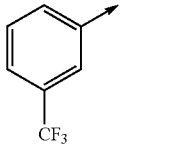 | Found MH⁺ 512 $C_{27}H_{28}{}^{81}BrNO_4$ requires 511 |
| 27 | A | 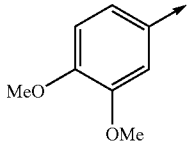 | Found MH⁺ 458<br>$C_{26}H_{26}F_3NO_3$ requires 457 |
| 28 | A |  | Found MH⁺ 450<br>$C_{27}H_{31}NO_5$ requires 449 |

TABLE 2-continued

[Structure: Ar-C(=O)-N(CH2-C6H3(OMe)(OMe))-CH2-CH(Me)-Ph]

| Example | Method | Ar | MS |
|---------|--------|----|----|
| 29 | A | 5-Me-1,2,4-oxadiazol-3-yl-phenyl (3-substituted) | Found MH$^+$ 472<br>C$_{28}$H$_{29}$N$_3$O$_4$ requires 471 |
| 30 | A | 2-(SO$_2$Me)-phenyl | Found MH$^+$ 468<br>C$_{26}$H$_{29}$NO$_5$S requires 467 |

TABLE 3

[Structure: Ar-C(=O)-N(CH2-C6H3(OMe)(Br))-CH2-CH(Me)-Ph]

| Example | Method | Ar | MS |
|---------|--------|----|----|
| 31 | A | —Ph | Found MH$^+$ 440<br>C$_{24}$H$_{24}$$^{81}$BrNO$_2$ requires 439 |
| 32 | A | 2-CN-phenyl | Found MH$^+$ 465<br>C$_{25}$H$_{23}$$^{81}$BrN$_2$O requires 464 |
| 33 | A | 2-(3-methyl-1,2,4-oxadiazol-5-yl)-phenyl | Found MH$^+$ 522<br>C$_{27}$H$_{26}$$^{81}$BrN$_3$O$_3$ requires 521 |

TABLE 3-continued

[Structure: Ar-C(=O)-N(CH2-C6H3(OMe)(Br))-CH2-CH(Me)-Ph]

| Example | Method | Ar | MS |
|---------|--------|----|----|
| 34 | A | 2,5-dimethoxyphenyl | Found MH$^+$ 500<br>C$_{26}$H$_{28}$$^{81}$BrNO$_4$ requires 499 |
| 35 | B | benzo[1,3]dioxol-5-yl | Found MH$^+$ 482<br>C$_{25}$H$_{24}$$^{79}$BrNO$_4$ requires 481 |
| 36 | B | 2-bromo-5-methoxyphenyl | Found MH$^+$ 546<br>C$_{25}$H$_{25}$$^{79}$Br$_2$NO$_3$ requires 545 |

TABLE 4

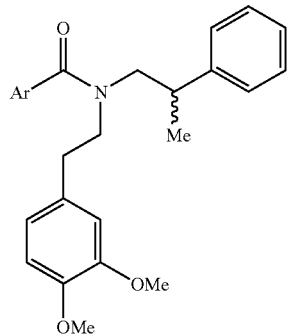

| Example | Method | Ar | MS |
|---|---|---|---|
| 37 | A | 3-bromophenyl | Found MH⁺ 484<br>$C_{26}H_{28}{}^{81}BrNO_3$ requires 483 |
| 38 | A | 2-cyanophenyl | Found MH⁺ 429<br>$C_{27}H_{28}N_2O_3$ requires 428 |
| 39 | A | 1-naphthyl | Found MH⁺ 454.<br>$C_{30}H_{31}NO_3$ requires 453 |
| 40 | A | 2-(3-methyl-1,2,4-oxadiazol-5-yl)phenyl | Found MH⁺ 486<br>$C_{29}H_{31}N_3O_4$ requires 485 |
| 41 | A | 2,3-dimethoxyphenyl | Found MH⁺ 464<br>$C_{28}H_{33}NO_5$ requires 463 |
| 42 | A | 3,5-dimethoxyphenyl | Found MH⁺ 464<br>$C_{28}H_{33}NO_5$ requires 463 |
| 43 | A | 2,4-dimethoxyphenyl | Found MH⁺ 464<br>$C_{28}H_{33}NO_5$ requires 463 |

TABLE 4-continued

| Example | Method | Ar | MS |
|---|---|---|---|
| 44 | A | 2,3-difluorophenyl | Found MH⁺ 440<br>$C_{26}H_{27}F_2NO_3$ requires 439 |

TABLE 5

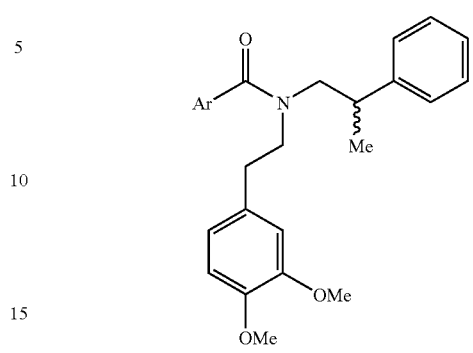

| Example | Method | Ar | MS |
|---|---|---|---|
| 45 | A | 5-bromo-2-methoxyphenyl | Found MH⁺ 534<br>$C_{26}H_{27}{}^{81}Br^{35}ClNO_4$ requires 533 |
| 46 | A | 5-bromo-2,3-dihydrobenzofuran-7-yl | Found MH⁺ 546<br>$C_{27}H_{27}{}^{81}Br^{35}ClNO_4$ requires 545 |
| 47 | A | 3-bromophenyl | Found MH⁺ 504<br>$C_{25}H_{25}{}^{81}Br^{35}ClNO_3$ requires 503 |

TABLE 5-continued

Structure: Ar-C(O)-N(CH2-[3,4-diMeO-phenyl])-CH2-CH(Me)-[4-Cl-phenyl]

| Example | Method | Ar | MS |
|---|---|---|---|
| 48 | A | 3-CF$_3$-phenyl | Found MH$^+$ 492<br>C$_{26}$H$_{25}$$^{35}$ClF$_3$NO$_3$ requires 491 |
| 49 | A | benzo[1,3]dioxol-5-yl | Found MH$^+$ 468<br>C$_{26}$H$_{26}$$^{35}$ClNO$_5$ requires 467 |

TABLE 6

Structure: Ar-C(O)-N(CH2-[4-MeO-3-Br-phenyl])-CH2-C(Me)$_2$-phenyl

| Example | Method | Ar | MS |
|---|---|---|---|
| 50 | A | —Ph | Found MH$^+$ 452<br>C$_{25}$H$_{26}$$^{79}$BrNO$_2$ requires 451 |
| 51 | A | 3-OMe-phenyl | Found MH$^+$ 484<br>C$_{26}$H$_{28}$$^{81}$BrNO$_3$ requires 483 |
| 52 | A | 2-(3-Me-1,2,4-oxadiazol-5-yl)phenyl | Found MH$^+$ 536<br>C$_{28}$H$_{28}$Br$^{81}$N$_3$O$_3$ requires 535 |

TABLE 7

Structure: Ar-C(O)-N(CH2-[4-MeO-3-Br-phenyl])-CH(Et)-phenyl

| Example | Method | Ar | MS |
|---|---|---|---|
| 53 | A | —Ph | Found MH$^+$ 454<br>C$_{25}$H$_{26}$$^{81}$BrNO$_2$ requires 453. |
| 54 | A | 3-OMe-phenyl | Found MH$^+$ 484<br>C$_{26}$H$_{28}$$^{81}$BrNO$_3$ requires 483. |
| 55 | A | 2-(3-Me-1,2,4-oxadiazol-5-yl)phenyl | Found MH$^+$ 534<br>C$_{25}$H$_{28}$$^{79}$BrN$_3$O$_3$ requires 533. |
| 56 | B | benzo[1,3]dioxol-5-yl | Found MH$^+$ 496<br>C$_{26}$H$_{26}$$^{79}$BrNO$_4$ requires 495. |

TABLE 8

Structure: Ar-C(O)-N(CH2-[3-OEt-4-MeO-phenyl])-CH(Me)-phenyl

| Example | Method | Ar | MS |
|---|---|---|---|
| 57 | A | 3-Br-phenyl | Found MH$^+$ 482<br>C$_{26}$H$_{28}$$^{79}$BrNO$_3$ requires 481 |

TABLE 8-continued

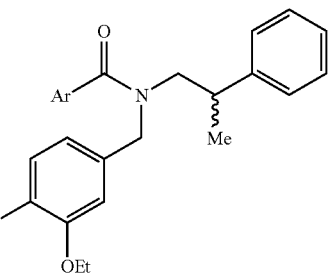

| Example | Method | Ar | MS |
|---|---|---|---|
| 58 | A | 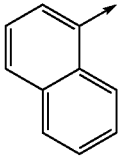 | Found MH+ 454<br>C$_{30}$H$_{31}$NO$_3$ requires 453 |
| 59 | A | 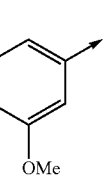 | Found MH+ 464<br>C$_{28}$H$_{33}$NO$_5$ requires 463 |
| 60 | A | 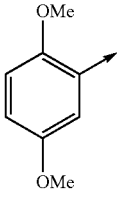 | Found MH+ 464<br>C$_{28}$H$_{33}$NO$_5$ requires 463 |

TABLE 9

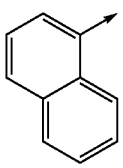

| Example | Method | Ar | MS |
|---|---|---|---|
| 61 | A | 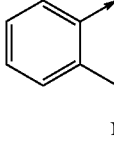 | Found MH+ 498<br>C$_{24}$H$_{26}$$^{81}$BrNO$_4$ requires 497 |

TABLE 9-continued

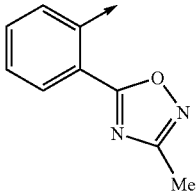

| Example | Method | Ar | MS |
|---|---|---|---|
| 62 | A | 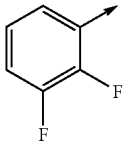 | Found MH+ 468<br>C$_{30}$H$_{29}$NO$_4$ requires 467 |
| 63 | A | 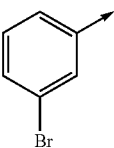 | Found MH+ 500<br>C$_{29}$H$_{29}$N$_3$O$_5$ requires 499 |
| 64 | A | 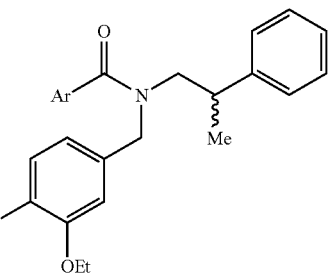 | Found MH+ 454<br>C$_{26}$H$_{25}$F$_2$NO$_4$ requires 453 |

TABLE 10

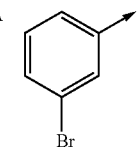

| Example | Method | Ar | MS |
|---|---|---|---|
| 65 | A | 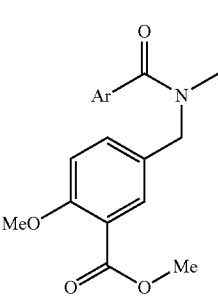 | Found MH+ 511.<br>C$_{25}$H$_{27}$$^{79}$BrN$_2$O$_4$ requires 510. |

TABLE 10-continued

| Example | Method | Ar | MS |
|---|---|---|---|
| 66 | A | 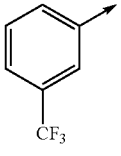 | Found MH+ 543. $C_{27}H_{29}{}^{81}BrN_2O_5$ requires 542. |
| 67 | A | 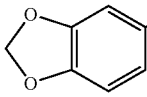 | Found MH+ 553. $C_{28}H_{29}{}^{79}BrN_2O_5$ requires 552. |
| 68 | A | (3-CF₃-phenyl) | Found MH+ 501. $C_{27}H_{27}F_3N_2O_4$ requires 500. |
| 69 | A | (benzo[1,3]dioxole) | Found MH+ 477. $C_{25}H_{25}N_2O_6$ requires 476. |

EXAMPLE 70

5-Bromo-2,3-dihydrobenzofuran-7-carboxylic acid (3,4-dimethoxy-benzyl)-(2-methyl-2-phenyl-propyl)-amide The title compound was prepared according to a procedure similar to that of Method A in Examples 1–69

MS (Electrospray LC/MS): Found MH+524. $C_{28}H_{30}{}^{79}BrNO_4$ requires 523.

EXAMPLE 71

(R,S)-3-Acetylamino-N-(3,4-dimethoxy-benzyl)-N-(2-phenyl-propyl)-benzamide

A solution of 3-acetylamino-benzoic acid (99 mg, 0.55 mmol) in DMF (5 ml) was treated sequentially with N,N-diisopropylethylamine (0.26 ml, 1.5 mmol), O-(7-azabenzotriazol-1-yl)-N,N,N',N'-tetramethyluronium hexafluorophosphate (HATU) (209 mg, 0.55 mmol) then (R,S)-(3,4-dimethoxy-benzyl)-(2-phenyl-propyl)-amine (D1b, 143 mg, 0.5 mmol) and then stirred at room temperature, under argon for 48 h. The reaction mixture was diluted with EtOAc then washed with saturated aqueous $K_2CO_3$, water (3×) then brine. The organic phase was dried ($MgSO_4$) and the solvent removed iii vacuo to afford the title compound as an orange gum (187 mg, 76%).

MS (Electrospray LC/MS): Found MH+447. $C_{27}H_{30}N_2O_4$ requires 446.

EXAMPLE 72

(R,S)-Benzothiazole-6-carboxylic acid (3,4-dimethoxy-benzyl)(2-phenyl-propyl)amide The title compound was prepared according to a procedure similar to that of Example 71.

MS (Electrospray LC/MS): Found MH+447. $C_{26}H_{26}N_2O_3S$ requires 446.

EXAMPLE 73

3-Acetylamino-N-(3-Bromo-4-methoxy-benzyl)-N-(2-methyl-2-phenyl-propyl)-benzamide The title compound was prepared according to a procedure similar to that of Example 71. Purifcation by chromatography (silica gel, 20–50% EtOAc-pentane) afforded the title compound.

MS (Electrospray LC/MS): Found MH+509. $C_{27}H_{29}{}^{79}BrN_2O_3$ requires 508.

EXAMPLE 74

(R,S)-Benzo[1,2,5]oxadiazole-5-carboxylic acid (3,4-dimethoxy-benzyl)-(2-phenyl-propyl)-amide The title compound was prepared according to a procedure similar to that of Example 71. The reaction mixture was heated at 50° C. in an attempt to effect completion. Unreacted amine was scavenged with isocyanate resin prior to the aqueous work-up described for Example 71. Purifcation by chromatography (silica gel, 0–20% EtOAc-pentane) afforded the title compound.

MS (Electrospray LC/MS): Found MH+432. $C_{25}H_{25}N_3O_4$ requires 431.

EXAMPLE 75

(R,S)-Benzo[1,2,5]thiadiazole-5-carboxylic acid (3,4-dimethoxy-benzyl)(2-phenyl-propyl)-amide The title compound was prepared according to a procedure similar to that of Example 71.

MS (Electrospray LC/MS): Found MH+448. $C_{25}H_{25}N_3O_3S$ requires 447.

EXAMPLE 76

(R,S)-Benzo[1,3]dioxole-5-carboxylic acid[2-(3,4-dimethoxy-phenyl)-ethyl]-2-phenyl-propyl) amide A stirring solution of benzo[1,3]dioxole-5-carbonyl chloride (138 mg, 0.75 mmol) in MDC (5 ml) was treated with a pre-mixed solution of (R,S)-[2-(3,4-dimethoxy-henyl) ethyl]-2-phenyl-propyl)amine (D1f, 224 mg, 0.75 mmol) and triethylamine (0.16 ml) in MDC (2 ml). After stirring under argon at room temperature for 2 h the reaction mixture was washed with water then brine. The organic phase was dried (MgSO$_4$) and the solvent removed in vacuo. The residue was chromatographed (silica gel, 20–800 EtOAc-pentane) to afford the title compound as a colourless gum (301 mg, 90%).

MS (API$^+$): Found MH$^+$448. C$_{27}$H$_{29}$NO$_5$ requires 447.

EXAMPLE 77

(R,S)-3-Bromo-N-(3-bromo-4-methoxy-benzyl)-N-2-phenyl-propyl)-benzamide

The title compound was prepared according to a procedure similar to that of Example 76

MS (Electrospray LC/MS): Found MH$^+$516. C$_{24}$H$_{23}$$^{79}$Br$_2$NO$_2$ requires 515.

EXAMPLE 78

(R,S)-2,2-Difluoro-benzo[1,3]dioxole-5-carboxylic acid[2-(3,4-dimethoxy-phenyl)-ethyl]-(2-phenyl-propyl)amide A solution of 2,2-difluorobenzo[1,3]dioxole-5-carboxylic acid (152 mg, 0.75 mmol) in DMF (5 ml) was treated sequentially with N,N-diisopropylethylamine (0.45 ml), O-(7-azabenzotriazol-1-yl)-N,N,N',N'-tetramethyluronium hexafluorophosphate (HATU) (285 mg, 0.75 mmol) then (R,S)-[2-(3,4-dimethoxy-phenyl)-ethyl]-(2-phenyl-propyl)-amine (D1f, 224 mg, 0.75 mmol) and then stirred at room temperature, under argon for 24 h. The reaction mixture was diluted with diethyl ether then washed with water (3x) then brine. The organic phase was dried (MgSO$_4$) and the solvent removed in vacuo. The residue was chromatographed (silica gel, 0–60% EtOAc-pentane) to afford the title compound as a yellow gum (300 mg, 83%).

MS (API$^+$LC/MS): Found MH$^+$484. C$_{27}$H$_{27}$F$_2$NO$_5$ requires 483.

EXAMPLE 79

(S)-3-Bromo-N-(3,4-dimethoxy-benzyl)-N-1-methyl-2-phenyl-ethyl)-benzamide

The title compound was prepared from 3-bromobenzoyl chloride and (S)(3,4-dimethoxybenzyl)1-methyl-2-phenylethyl)amine, D7 according to a procedure similar to that for Example 76.

MS (Electrospray LC/MS): Found MH$^+$468. C$_{25}$H$_{26}$$^{79}$BrNO$_3$ requires 467.

EXAMPLE 80

(S)-3-Bromo-N-[2-(3,4-dimethoxy-phenyl)-ethyl]-N-(1-methyl-2-phenyl-ethyl)-benzamide The title compound was prepared from 3-bromobenzoyl chloride and (S)-[2-(3,4 dimethoxyphenyl)ethyl]-(1-methyl-2-phenylethyl)amine D8 according to a procedure similar to that for Example 76.

MS (Electrospray LC/MS): Found MH$^+$482. C$_{26}$H$_{28}$$^{79}$BrNO$_3$ requires 481.

EXAMPLE 81

(S)-Benzo[1,3]dioxol-5-carboxylic acid [2-(3,4-dimethoxy-phenyl)ethyl]-(1-methyl-2-phenylethyl)-amide The title compound was prepared from benzo[1,3]dioxole-5-arbonyl chloride and (S)[2-(3,4-dimethoxyphenyl)ethyl]-1-methyl-2-phenylethyl)amine, D8 according to a procedure similar to that for Example 76.

MS (Electrospray LC/MS): Found MH$^+$448. C$_{27}$H$_{29}$NO$_5$ requires 447.

EXAMPLE 82

(R)-Benzo[1,3]dioxole-5-carboxylic acid [2-(3,4-dimethoxy-phenyl)-ethyl]-(2-phenyl-propyl)-amide A stirring solution of benzo[1,3]dioxole-5-carbonyl chloride (151 mg, 0.82 mmol) in MDC (5 ml) was treated with a pre-mixed solution of (R)-[2-(3,4-dimethoxy-phenyl)-ethyl]-(2-phenyl-propyl)-amine (D12, 245 mg, 0.75 mmol) and triethylamine (0.17 ml) in MDC (2 ml). After stirring under argon at room temperature for 72 h the solvent was removed in vacuo and the residue was chromatographed (silica gel, 0–40% EtOAc-pentane) to afford the title compound as a colourless gum (250 mg, 68%).

MS (Electrospray LC/MS): Found MH$^+$448. C$_{27}$H$_{29}$NO$_5$ requires 447.

$^1$H NMR T=360K (D$_6$-DMSO) δ: 1.20 (3H, d, J=7 Hz), 2.66 (2H, t, J=7 Hz), 3.17 (1H, m), 3.28 (1H, m), 3.42 (1H, m), 3.48 (1H, m), 3.56 (1H, m), 3.71 (3H, s), 3.73 (3H, s), 6.0 (2H, s), 6.48 (1H, d), 6.56 (1H, d), 6.59 (2H, m), 6.83 (1H, d, J=8 Hz), 6.85 (1H, d, J=8 Hz), 7.22 (3H, m), 7.30 (2H, m).

EXAMPLE 83

(R)-2-Cyan-N-[2-(3,4-dimethoxy-phenyl)ethyl]-N-(2-phenyl-propyl)-benzamide)

A stirring solution of 2-cyano-benzoic acid (120 mg, 0.82 mmol) in MDC (5 ml) was treated with oxalyl chloride (0.22 ml, 2.5 mmol) and DMF (1 drop). After 2 h the volatiles were removed in vacuo and the residue was triturated with toluene (2x). The residue was dissolved in MDC (5 ml) and treated with a pre-mixed solution of (R)-[2-(3,4-dimethoxy-phenyl)-ethyl]-2-phenyl-propyl)amine (D12, 245 mg, 0.82 mmol) and trietlyamine (0.17 ml) in MDC (5 ml). After stirring under argon at room temperature for 72 h the solvent was removed in vacuo and the residue was chromatographed (silica gel, 040% EtOAc-pentane) to afford the title compound as a colourless gum (220 mg, 63%)

MS (Electrospray LC/MS): Found MH$^+$429. C$_{27}$H$_{28}$N$_2$O$_3$ requires 428.

$^1$HNMR δ: 1.14 (1.5H, d, J=7 Hz), 1.42 (1.5H, d, J=7 Hz), 2.56 (1H, m), 2.87–3.10 (2H, bm), 3.16–3.42 (2H, bm), 3.52 (0.5H, m), 3.604.00 (7.5H, bm), 6.25 (0.5H, d, J=2 Hz), 6.39

(0.5H, dd, J=2 and 10 Hz), 6.72 (1H, m), 6.85 (2H, m), 6.92 (1H, m), 7.25 (2H, m), 7.32–7.52 (4H, m), 7.65 (1H, m).

The following compounds in Examples 84–91 were prepared by a procedure similar to that for Example 76.

TABLE 11

| Example | Ar | MS |
|---|---|---|
| 84 | 3-bromophenyl | Found MH$^+$ 480<br>$C_{26}H_{26}^{79}BrNO_3$ requires 479 |
| 85 | benzo[1,3]dioxol-5-yl | Found MH$^+$ 446<br>$C_{27}H_{27}NO_5$ requires 445 |
| 86 | 1-naphthyl | Found MH$^+$ 452<br>$C_{30}H_{29}NO_3$ requires 451 |
| 87 | 2,3-difluorophenyl | Found MH$^+$ 438<br>$C_{24}H_{25}F_2NO_3$ requires 437 |
| 88 | 2-OMe-4-Br-phenyl | Found MH$^+$ 510<br>$C_{27}H_{28}^{79}BrNO_4$ requires 509 |
| 89 | 2-cyanophenyl | Found MH$^+$ 427<br>$C_{27}H_{26}N_2O_3$ requires 426 |

TABLE 12

| Example | Ar | MS |
|---|---|---|
| 90 | benzo[1,3]dioxol-5-yl | Found MH$^+$ 429<br>$C_{26}H_{24}N_2O_4$ requires 428 |
| 91 | 1-naphthyl | Found MH$^+$ 435<br>$C_{29}H_{26}N_2O_2$ requires 434 |

Examples 92–104 were prepared from the appropriate amine and carboxylic acid according to Method C or Method D.

METHOD C

A solution of the carboxylic acid in DMF (2 ml/mmol) was treated sequentially with N,N-diisopropylethylamine (3 eq.), O-7-azabenzotriazol-1-yl)-N,N,N',N'-tetramethyluronium hexafluorophosphate (HATU) (1 eq.) then after 20 min. the appropriate amine (1 eq.) and then stirred at room temperature, under argon for 16 h. The reaction mixture was diluted with diethyl ether then washed with water (2×) then brine. The organic phase was dried (MgSO$_4$) and the solvent removed in vacuo. Purification was carried out as required by chromatography on silica gel.

METHOD D

A solution of the carboxylic acid in MDC (10 ml/mmol) was treated with oxalyl chloride (3 eq.) then DMF (1 drop). After stirring at room temperature for 2.5 h the volatiles were removed in vacuo. The residue was azeotroped with toluene then redissolved in MDC (10 ml/mmol). Triethylamine (1.1 eq.) and the appropriate amine (1 eq.) in MDC (5 ml/mmol) were added and the solution was stirred at room temperature for 16 h. The reaction mixture was diluted with MDC then washed with aqueous NaHCO$_3$ (2×) then brine. The organic phase was dried (MgSO$_4$) and the solvent removed in vacuo. Purification was carried out as required by chromatography on silica gel.

TABLE 13

[Structure: Ar-C(=O)-N(CH2-C6H3(OMe)2)-CH2-CH(Me)-Ph]

| Example | Method | Ar | MS |
|---|---|---|---|
| 92 | C | isoquinolin-8-yl | Found MH⁺ 441<br>$C_{28}H_{28}N_2O_3$ requires 440 |
| 93 | C | quinolin-8-yl | Found MH⁺ 441<br>$C_{28}H_{28}N_2O_3$ requires 440 |
| 94 | C | 2-methylquinolin-4-yl | Found MH⁺ 455<br>$C_{29}H_{30}N_2O_3$ requires 454 |
| 95 | C | 2-methylquinolin-5-yl | Found MH⁺ 455<br>$C_{29}H_{30}N_2O_3$ requires 454 |

TABLE 14

[Structure: Ar-C(=O)-N(CH2CH2-C6H3(OMe)2)-CH2-CH(Me)-Ph]

| Example | Method | Ar | MS |
|---|---|---|---|
| 96 | D | 5-(4-fluorophenyl)-2-methylthiazol-4-yl | Found MH⁺ 519<br>$C_{30}H_{31}FN_2O_3S$ requires 518 |
| 97 | D | 5-(4-fluorophenyl)thiazol-4-yl | Found MH⁺ 505<br>$C_{29}H_{29}FN_2O_3S$ requires 504 |
| 98 | D | 5-(2-fluorophenyl)-2-methylthiazol-4-yl | Found MH⁺ 519<br>$C_{30}H_{31}FN_2O_3S$ requires 518 |
| 99 | D | 5-(2-fluorophenyl)-2-methyl-2H-1,2,3-triazol-4-yl | Found MH⁺ 503<br>$C_{29}H_{31}FN_4O_3$ requires 502 |

TABLE 14-continued

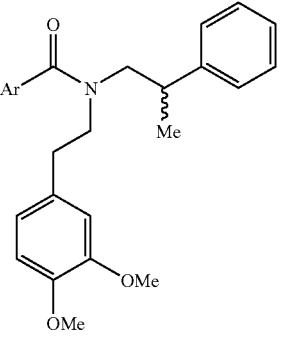

| Example | Method | Ar | MS |
|---|---|---|---|
| 100 | C | 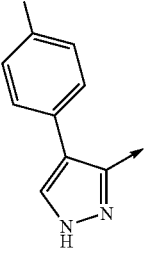 | Found MH+ 488 $C_{29}H_{30}FN_3O_3$ requires 487 |
| 101 | D | 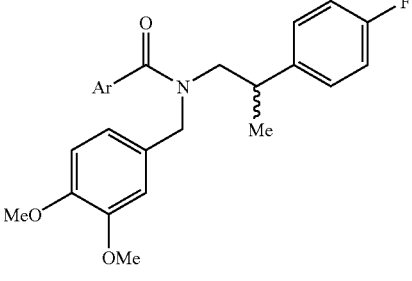 | Found MH+ 512 $C_{17}H_{30}{}^{79}BrNO_4$ requires 511 |

TABLE 15

| Example | Method | Ar | MS |
|---|---|---|---|
| 102 | C | 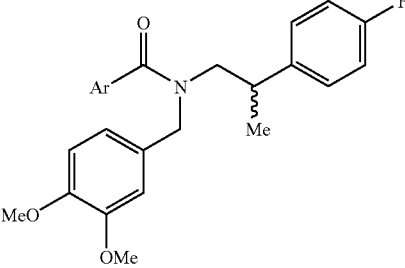 | Found MH+ 452 $C_{26}H_{26}FNO_5$ requires 451 |
| 103 | C | 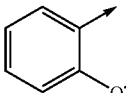 | Found MH+ 433 $C_{26}H_{25}FN_2O_3$ requires 432 |

TABLE 15-continued

| Example | Method | Ar | MS |
|---|---|---|---|
| 104 | C |  | Found MH+ 495 $C_{29}H_{35}FN_2O_4$ requires 494 |

EXAMPLE 105

(R,S)-N-(2-Benzoylamino-propyl)-3-bromo-N-[2-(3,4-dimethoxy-phenyl)-ethyl]-benzamide A stirring solution of 3-bromobenzoyl chloride (0.042 ml, 0.32 mmol) in MDC (5 ml) was treated with a pre-mixed solution of (R,S)-N-{2-[2-(3,4-dimethoxy-phenyl)ethylamino]-1-methyl-ethyl}-benzamide, D17 (100 mg, 0.32 mmol) and triethylamine (0.045 ml, 0.32 mmol) in MDC (7 ml). After stirring under argon at room temperature for 72 h the reaction mixture was washed with aqueous NaHCO$_3$ then brine. The organic phase was dried (MgSO$_4$) and the solvent removed in vacuo. The residue was chromatographed (silica gel, 0–50% EtOAc-pentane) to afford the title compound as a yellow gum (60 mg, 39%).

MS (API$^+$LC/MS): Found MH$^+$527. $C_{27}H_{29}{}^{81}BrN_2O_4$ requires 526.

EXAMPLE 106

(R,S)-N-(2-Benzoylamino-propyl)-5-bromo-N-[2-(3,4-dimethoxy-phenyl)-ethyl]-2-methoxybenzamide The title compound was prepared from of (R,S)-N-{2-[2-(3,4-dimethoxy-phenyl)-ethylamino]-1-methyl-ethyl}-benzamide, D17 according to a procedure similar to that of Example 105.

MS (API$^+$LC/MS): Found MH$^+$557. $C_{28}H_{31}{}^{81}BrN_2O_5$ requires 556.

EXAMPLE 107

(S)-3-Bromo-N-(3,4-dimethoxy-benzyl)-N-(2-phenylpropyl)-benzamide

The title compound was prepared from (S)-3,4-dimethoxy-benzyl)-(2-phenyl-propyl)-amine, D22 according to a procedure similar to that of Example 76.

MS (API$^+$ LC/MS): Found MH$^+$468. $C_{25}H_{26}{}^{79}BrNO_3$ requires 467.

It is to be understood that the present invention covers all combinations of particular and preferred subgroups described herein above.

Determination of Orexin-1 Receptor Antagonist Activity

The orexin-1 receptor antagonist activity of the compounds of formula (I) was determined in accordance with the following experimental method.

Experimental Method

HEK293 cells expressing the human orexin-1 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 µl/well into 96-well black clear bottom sterile plates from Costar which had been precoated with 10 µg/well of poly-L-lysine from SIGMA. The seeded plates were incubated overnight at 37° C. in 5% $CO_2$.

Agonists were prepared as 1 mM stocks in water:DMSO (1:1). $EC_{50}$ values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist $IC_{50}$ values (the concentration of compound needed to inhibit 50% of the agonist response) were determined against 3.0 nM human orexin-A using 11× half log unit dilutions in Tyrode's buffer containing 10% DMSO and probenecid.

On the day of assay 50 µl of cell medium containing probenecid (Sigma) and Fluo3AM (Texas Fluorescence Laboratories) was added (Quadra, Tomtec) to each well to give final concentrations of 2.5 mM and 4 µM, respectively. The 96-well plates were incubated for 90 min at 37° C. in 5% $CO_2$. The loading solution containing dye was then aspirated and cells were washed with 4×150 µl Tyrode's buffer containing probenecid and 0.1% gelatin (Denley Cell Wash). The volume of buffer left in each well was 125 µl. Antagonist or buffer (25 µl) was added (Quadra) the cell plates gently shaken and incubated at 37° C. in 5% $CO_2$ for 30 min. Cell plates were then transferred to the Fluorescent Imaging Plate Reader (FLIPR, Molecular Devices) instrument and maintained at 37° C. in humidified air. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1–19 inclusive was subtracted from this figure. The peak increase in fluorescence was plotted against compound concentration and iteratively curve fitted using a four parameter logistic fit (as described by Bowen and Jerman, *TiPS*, 1995, 16, 413417) to generate a concentration effect value. Antagonist Kb values were calculated using the equation:

$$K_b = IC_{50}/(1+([3/EC_{50}])$$

where $EC_{50}$ was the potency of human orexin-A determined in the assay (in nM terms) and $IC_{50}$ is expressed in molar terms.

Determination of Orexin-2 Receptor Antagonist Activity

The orexin-2 receptor antagonist activity of the compounds of formula (I) was determined in accordance with the following experimental method.

Experimental Method

CHO-DG44 cells expressing the human orexin-2 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 µl/well into 96-well black clear bottom sterile plates from Costar which had been pre-coated with 10 µg/well of poly-L-lysine from SIGMA. The seeded plates were incubated overnight at 37 C in 5% $CO_2$.

Agonists were prepared as 1 mM stocks in water:DMSO (1:1). $EC_{50}$ values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist $IC_{50}$ values (the concentration of compound needed to inhibit 50% of the agonist response) were determined against 10.0 nM human orexin-A using 11× half log unit dilutions in Tyrode's buffer containing 10% DMSO and probenecid.

On the day of assay 50 µl of cell medium containing probenecid (Sigma) and Fluo3AM (Texas Fluorescence Laboratories) was added (Quadra, Tomtec) to each well to give final concentrations of 2.5 mM and 4 µM, respectively. The 96-well plates were incubated for 60 min at 37 C in 5% $CO_2$. The loading solution containing dye was then aspirated and cells were washed with 4×150 µl Tyrode's buffer containing probenecid and 0.1% gelatin (Denley Cell Wash). The volume of buffer left in each well was 125 µl. Antagonist or buffer (25 µl) was added (Quadra) the cell plates gently shaken and incubated at 37 C in 5% $CO_2$ for 30 min. Cell plates were then transferred to the Fluorescent Imaging Plate Reader (FLIPR, Molecular Devices) instrument Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1–19 inclusive was subtracted from this figure. The peak increase in fluorescence was plotted against compound concentration and iteratively curve fitted using a four parameter logistic fit (as described by Bowen and Jennan, *TiPS*, 1995, 16, 413417) to generate a concentration effect value. Antagonist Kb values were calculated using the equation:

$$Kb = IC_{50}/(1+([3/EC_{50}])$$

where $EC_{50}$ was the potency of human orexin-A determined in the assay (in nM terms) and $IC_{50}$ is expressed in molar terms.

All compounds of Examples 1–107 tested according to these methods had pKb values of at least 7.0 at one or both of the human cloned orexin-1 receptor and the human cloned orexin-2 receptor.

No toxicological effects are indicated/expected when a compound (of the invention) is administered in the above mentioned dosage range.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The invention claimed is:

1. A compound of formula (I):

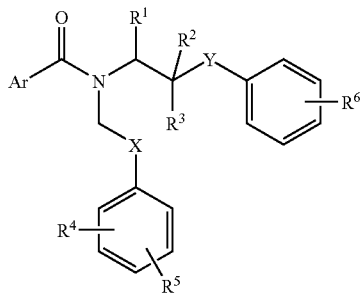

wherein:
R$^1$ is hydrogen; R$^2$ is (C$_{1-3}$)alkyl; and R$^3$ is hydrogen or (C$_{1-3}$)alkyl; or R$^2$ and R$^3$ together with the carbon to which they are attached form a (C$_{3-5}$) cycloalkyl group; or R$^1$ is (C$_{1-3}$)alkyl; R$^2$ is hydrogen; and R$^3$ is hydrogen, or (C$_{1-3}$)alkyl;

R$^4$ and R$^5$ are independently selected from hydrogen, halogen, NC—, optionally substituted (C$_{1-6}$)alkylCO, optionally substituted (C$_{1-6}$)alkyl, optionally substituted (C$_{1-6}$)alkoxy, optionally substituted (C$_{1-6}$)alkylOCO—, and optionally substituted (C$_{1-6}$)alkylNHCO—; provided that R$^4$ and R$^5$ are not both hydrogen;

R$^6$ is hydrogen or halogen;

Ar represents an optionally substituted aryl or an optionally substituted 5- or 6-membered aromatic heterocyclyl group containing up to 3 heteroatoms selected from N, O and S; or Ar represents an optionally substituted bicyclic heteroaryl group containing up to 3 heteroatoms selected from N, O and S;

wherein said optionally substituted Ar is substituted by 1 to 3 substituents independently selected from the group consisting of: phenyl optionally substituted by halogen; a 5- or 6-membered aromatic heterocyclyl group containing up to 3 heteroatoms selected from N, O and S, optionally substituted by (C$_{1-4}$)alkyl; halogen; hydroxy; oxo; cyano; nitro; (C$_{1-4}$)alkyl; hydroxy(C$_{1-4}$)alkyl; (C$_{1-4}$)alkoxy; hydroxy(C$_{1-4}$)alkoxy; halo(C$_{1-4}$)alkyl; halo(C$_{1-4}$)alkoxy; aryl(C$_{1-4}$)alkoxy; (C$_{1-4}$)alkylthio; hydroxy(C$_{1-4}$)alkyl; (C$_{1-4}$)alkoxy(C$_{1-4}$)alkyl; (C$_{3-6}$)cycloalkyl(C$_{1-4}$)alkoxy; (C$_{1-4}$)alkanoyl; (C$_{1-4}$)alkoxycarbonyl; (C$_{1-4}$)alkylsulfonyl; (C$_{1-4}$)alkylsulfonyloxy; (C$_{1-4}$)alkylsulfonyl(C$_{1-4}$)alkyl; arylsulfonyl; arylsulfonyloxy; arylsulfonyl(C$_{1-4}$)alkyl; (C$_{1-4}$)alkylsulfonamido; (C$_{1-4}$)alkylamido; (C$_{1-4}$)alkylsulfonamido(C$_{1-4}$)alkyl; (C$_{1-4}$)alkylamido(C$_{1-4}$)alkyl; arylsulfonamido; arylcarboxamido; arylsulfonamido(C$_{1-4}$)alkyl; arylcarboxamido(C$_{1-4}$)alkyl; aroyl; aroyl(C$_{1-4}$)alkyl; aryl(C$_{1-4}$)alkanoyl group; and a group R$^x$R$^y$N—, R$^x$OCO(CH$_2$)$_r$, R$^x$CON(R$^y$)(CH$_2$)$_r$, R$^x$R$^y$NCO(CH$_2$)$_r$, R$^x$R$^y$N(CH$_2$)$_r$O, R$^x$R$^y$NSO$_2$(CH$_2$)$_r$ or R$_x$SO$_2$NR$^y$(CH$_2$)$_r$ where each of R$^x$ and R$^y$ independently represents a hydrogen atom or a (C$_{1-4}$)alkyl group or where appropriate R$^x$R$^y$ forms part of a (C$_{3-6}$)azacycloalkane or (C$_{3-6}$)(2-oxo)azacycloalkane ring and r represents zero or an integer from 1 to 4;

wherein when Ar is phenyl, two substituents on adjacent carbon atoms may, together with the ring to which they are attached, form a bicyclic or tricyclic heterocyclyl or carbocyclyl ring system, which may be optionally substituted by halogen or oxo;

X is —CH$_2$—, or a bond; Y is —NHCO—, or a bond; or a pharmaceutically acceptable salt or solvate thereof.

2. A compound according to claim 1 wherein R$^1$ is hydrogen and R$^2$ and R$^3$ are selected from the combinations: methyl/hydrogen, ethyl/hydrogen and methyl/methyl.

3. A compound according to claim 1 wherein Ar is phenyl, naphthyl, furanyl, thienyl, pyrrolyl, oxazolyl, thiazolyl, imidazolyl, oxadiazolyl, thiadiazolyl, triazolyl, triazinyl, pyridazyl, pyrimidinyl, isothiazolyl, isoxazolyl, pyrazinyl, pyrazolyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzothiadiazolyl or naphthyridinyl, any of which may be optionally substituted.

4. A compound according to claim 1 wherein Ar is phenyl, naphthyl, quinolinyl, isoquinolinyl, benzothiazolyl, benzoxadiazolyl, benzothiadiazolyl, thiazolyl, triazolyl, or pyrazolyl, any of which may be optionally substituted.

5. A compound selected from:
(R)-benzo[1,3]dioxole-5-carboxylic acid[2-(3,4-dimethoxy-phenyl)-ethyl]-(2-phenyl-propyl)-amide;

(R)-2-cyano-N-[2-(3,4-dimethoxy-phenyl)-ethyl]-N-(2-phenyl-propyl)-benzamide) and a pharmaceutically acceptable salt or solvate of either thereof.

6. A pharmaceutical composition comprising a compound of formula (I) as defined in claim 1, or a pharmaceutically acceptable salt or solvate thereof, and a pharmaceutically acceptable carrier.

7. A method of treating diseases or disorders where an antagonist of a human orexin receptor is required, which comprises administering to a subject in need thereof an effective amount of a compound of formula (I) as defined in claim 1, or a pharmaceutically acceptable salt or solvate thereof.

8. A process for the preparation of a compound of formula (I), or a pharmaceutically acceptable salt or solvate thereof, according to claim 1 which process comprises reacting a compound of formula (II) with a compound of formula (III):

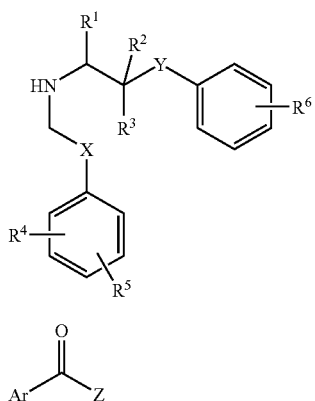

wherein Ar, $R^1$, $R^2$, $R^3$, $R^4$, $R^5$, $R^6$, X and Y are as hereinbefore defined for compounds of formula (I), and Z is a leaving group or a group converted to a leaving group in-situ followed by, optional, conversion to a pharmaceutically acceptable salt or solvate thereof.

9. A compound according to claim 1 having the formula selected from the group consisting of:

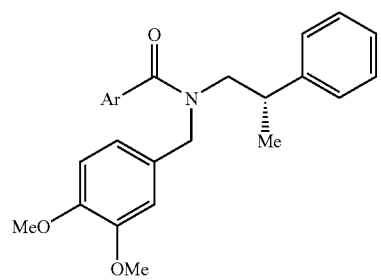

wherein Ar is

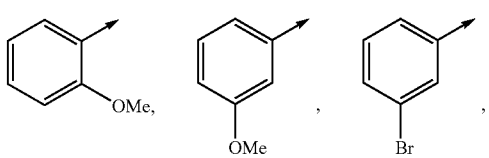

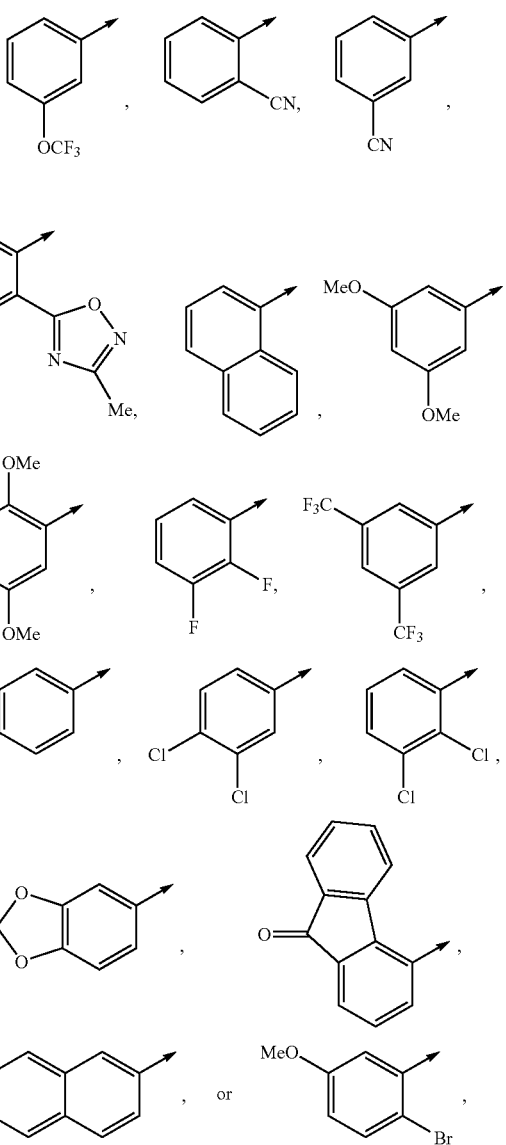

and a pharmaceutically acceptable salt or solvate of any one thereof.

10. A compound according to claim 1 having a formula selected from the group consisting of:

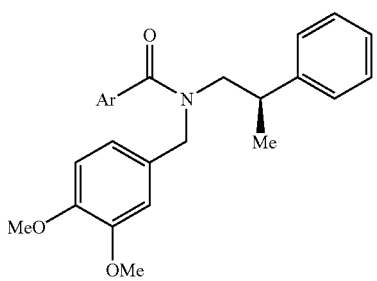

wherein Ar is

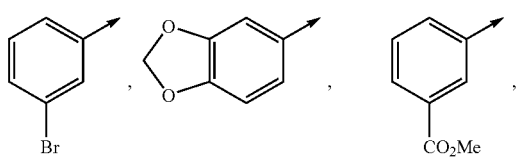

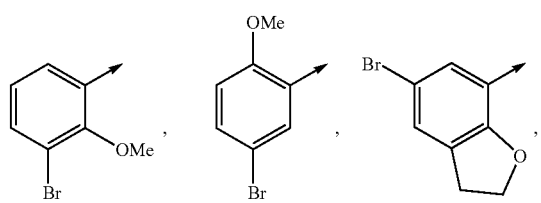

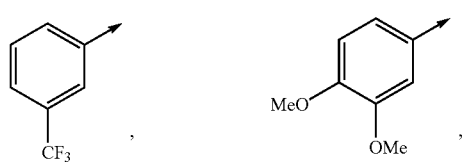

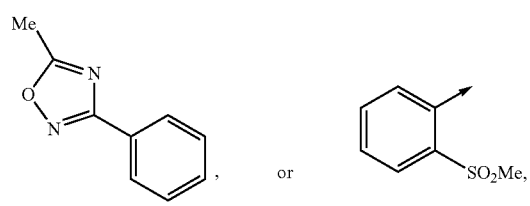

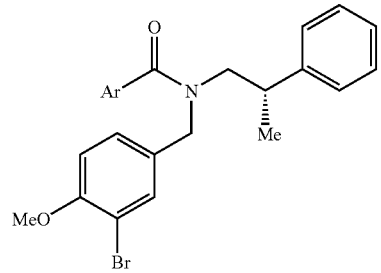

and a pharmaceutically acceptable salt or solvate of any one thereof.

11. A compound according to claim 1 having the formula selected from the group consisting of:

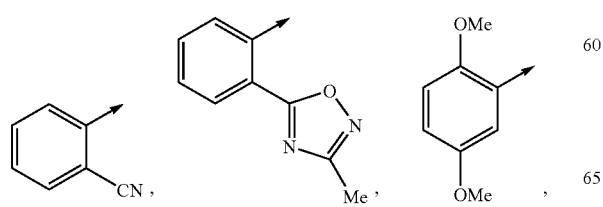

wherein Ar is

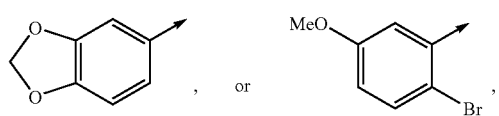

-continued

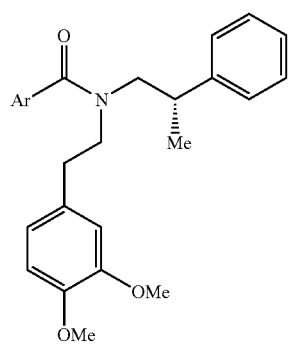

and a pharmaceutically acceptable salt or solvate of any one thereof.

12. A compound according to claim 1 having the formula selected from the group consisting of:

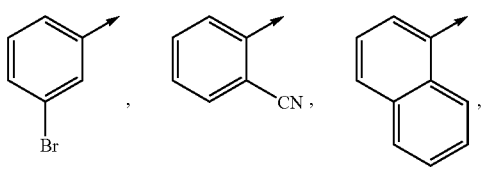

wherein Ar is

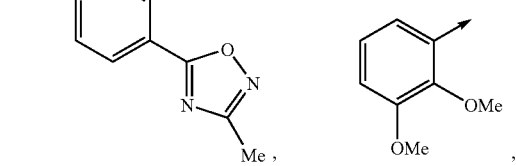

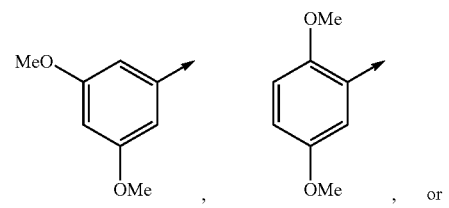

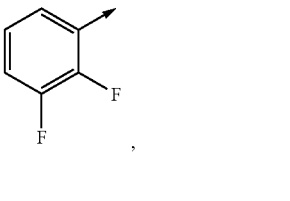

13. A compound according to claim 1 having the formula selected from the group consisting of:

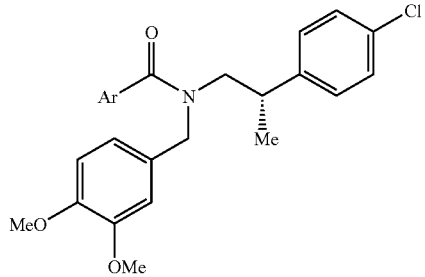

wherein Ar is

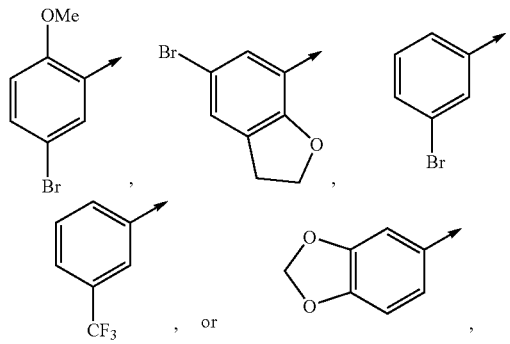

and a pharmaceutically acceptable salt or solvate of any one thereof.

14. A compound according to claim 1 having the formula selected from the group consisting of:

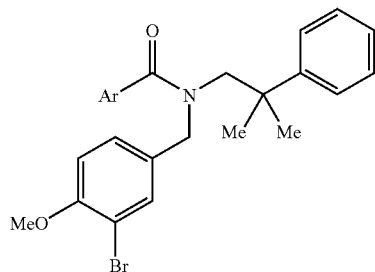

wherein Ar is

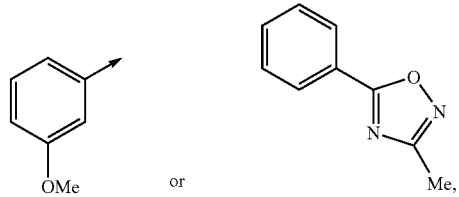

15. A compound according to claim 1 having the formula selected from the group consisting of:

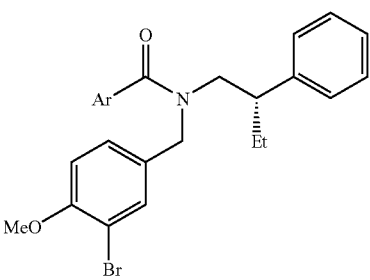

wherein Ar is

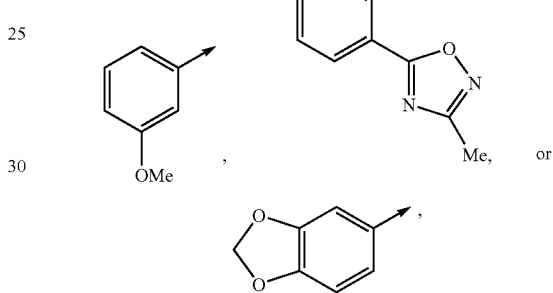

and a pharmaceutically acceptable salt or solvate of any one thereof.

16. A compound according to claim 1 having the formula selected from the group consisting of:

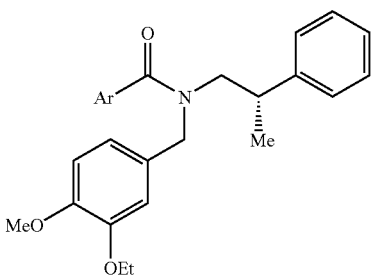

wherein Ar is

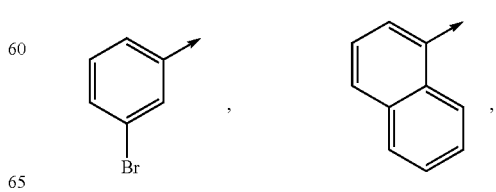

-continued

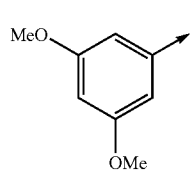, or 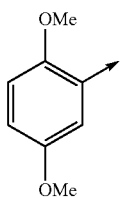, and a pharmaceutically acceptable salt or solvate of any one thereof.

17. A compound according to claim 1 having the formula selected from the group consisting of:

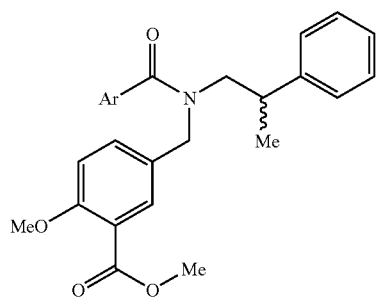

wherein Ar is

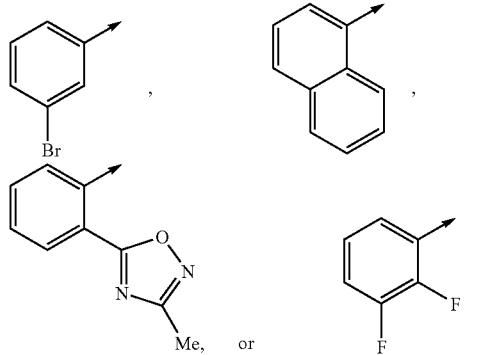

and a pharmaceutically acceptable salt or solvate of any one thereof.

18. A compound according to claim 1 having the formula selected from the group consisting of:

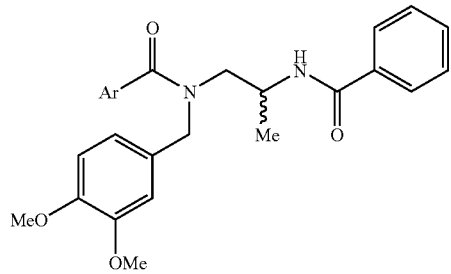

wherein Ar is

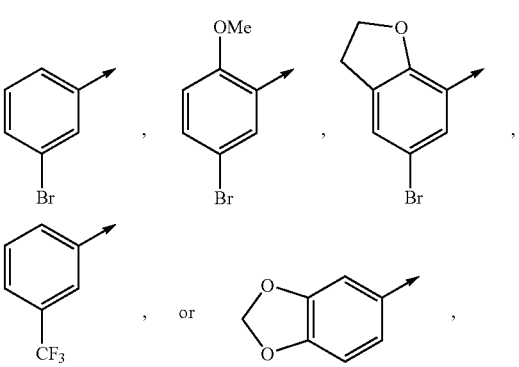

and a pharmaceutically acceptable salt or solvate of any one thereof.

19. A compound according to claim 1 having the formula selected from the group consisting of:

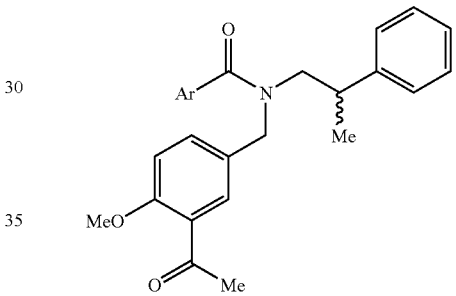

wherein Ar is

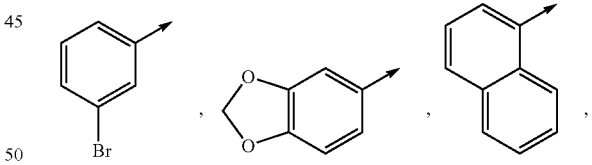

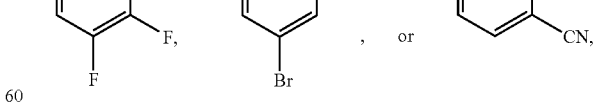

and a pharmaceutically acceptable salt or solvate of any one thereof.

20. A compound according to claim 1 having the formula selected from the group consisting of:

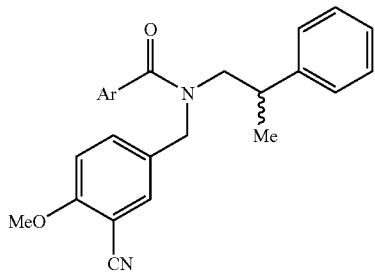

wherein Ar is

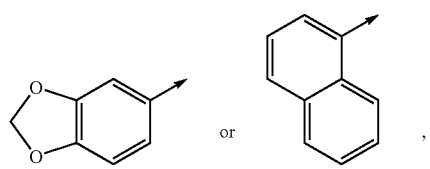

and a pharmaceutically acceptable salt or solvate of any one thereof.

21. A compound according to claim 1 having the formula selected from the group consisting of:

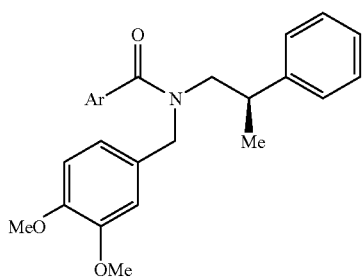

wherein Ar is

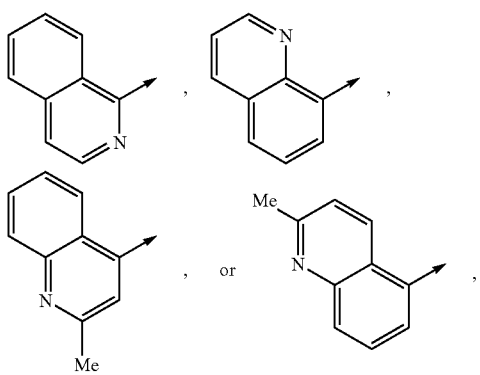

and a pharmaceutically acceptable salt or solvate of any one thereof.

22. A compound according to claim 1 having the formula selected from the group consisting of:

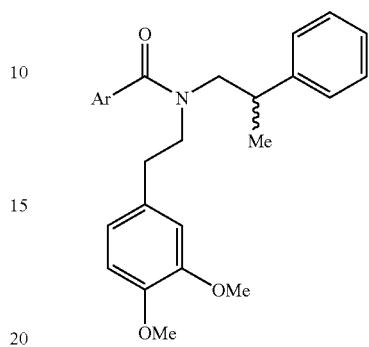

wherein Ar is

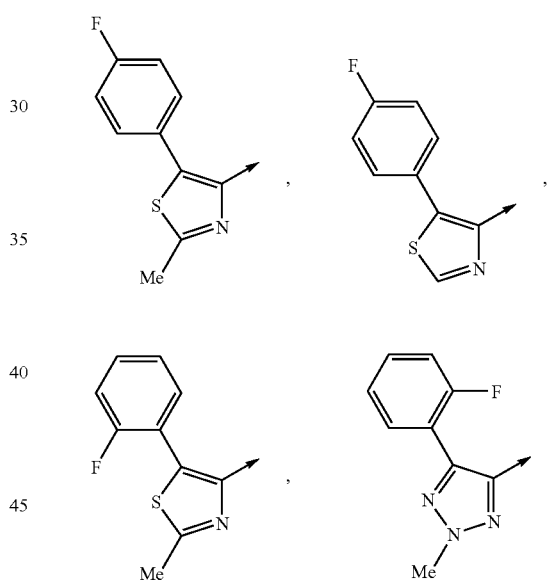

and a pharmaceutically acceptable salt or solvate of any one thereof.

23. A compound according to claim 1 having the formula selected from the group consisting of:

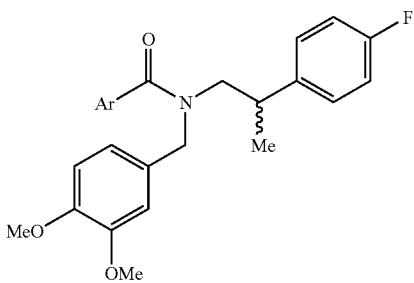

wherein Ar is

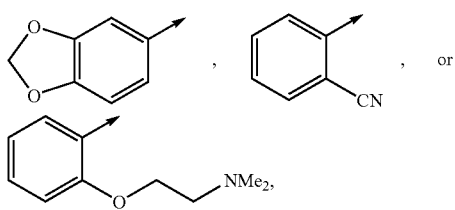

and a pharmaceutically acceptable salt or solvate of any one thereof.

24. A compound according to claim 1 selected from the group consisting of: 5-bromo-2,3-dihydrobenzofuran-7-carboxylic acid (3,4-dimethoxy-benzyl)-(2-methyl -2-phenyl-propyl)-amide;
   (R,S)-3-acetylamino-N-(3,4-dimethoxy-benzyl)-N-(2-phenyl-propyl)-benzamide;
   (R,S)-benzothiazole-6-carboxylic acid (3,4-dimethoxy-benzyl)-(2-phenyl-propyl)-amide;
   3-acetylamino-N-(3-bromo-4-methoxy-benzyl)-N-(2-methyl-2-phenyl-propyl)-benzamide;
   (R,S)-benzo[1,2,5]oxadiazole-5-carboxylic acid (3,4-dimethoxy-benzyl)-(2-phenyl-propyl)-amide;
   (R,S)-benzo[1,2,5]thiadiazole-5-carboxylic acid (3,4-dimethoxy-benzyl)-(2-phenyl-propyl)-amide;
   (R,S)-benzo[1,3]dioxole-5-carboxylic acid [2-(3,4-dimethoxy-phenyl)-ethyl]-(2-phenyl-propyl) amide;
   (R,S)-3-bromo-N-(3-bromo-4-methoxy-benzyl) -N-(2-phenyl-propyl)-benzamide;
   (R,S)-2,2-difluoro-benzo[1,3]dioxole-5-carboxylic acid [2-(3,4-dimethoxy-phenyl)-ethyl]-(2-phenyl-propyl) amide;
   (S)-3-bromo-N-(3,4-dimethoxy-benzyl) -N-1-methyl-2-phenyl-ethyl)-benzamide;
   (S)-3-bromo-N-[2-(3,4-dimethoxy-phenyl) -ethyl]-N-(1-methyl-2-phenyl-ethyl)-benzamide;
   (S)-benzo[1,3]dioxol-5-carboxylic acid [2-(3,4-dimethoxy-phenyl)-ethyl]-(1-methyl-2-phenyl-ethyl)-amide;
   (R)-benzo[1,3]dioxole-5-carboxylic acid[2-(3,4-dimethoxy-phenyl)-ethyl]-(2-phenyl-propyl)-amide;
   (R)-2-cyanoN-[2-(3,4-dimethoxy-phenyl)-ethyl]-N-(2-phenyl-propyl)-benzamide);
   and a pharmaceutically acceptable salt or solvate of any one thereof.

25. A compound according to claim 1 selected from the group consisting of:
   (R,S)-N-(2-benzoylamino-propyl)-3-bromo-N-[2-(3,4-dimethoxy-phenyl)-ethyl]-benzainide;
   (R,S)-N-(2-benzoylamino-propyl)-5-bromo-N-[2-(3,4-dimethoxy-phenyl)-ethyl]-2-methoxy-benzamide;
   (S)-3-bromo-N-(3,4-dimethoxy-benzyl)-N-(2-phenyl-propyl)-benzamide;
   and a pharmaceutically acceptable salt or solvate of any one thereof.

* * * * *

SEQUENCE LISTING

<160> NUMBER OF SEQ ID NOS: 1

<210> SEQ ID NO 1
<211> LENGTH: 35
<212> TYPE: PRT
<213> ORGANISM: Homo sapien

<400> SEQUENCE: 1

Glu Pro Leu Pro Asp Cys Cys Arg Gln Lys Thr Cys Ser Cys Arg Leu
 1               5                  10                  15

Tyr Glu Leu Leu His Gly Ala Gly Asn His Ala Ala Gly Ile Leu Thr
            20                  25                  30

Leu Asn His
        35